United States Patent
Okada et al.

[11] Patent Number: 6,057,482
[45] Date of Patent: May 2, 2000

[54] PROCESS FOR PRODUCING BENZYL ACETATE AND BENZYL ALCOHOL

[75] Inventors: Takashi Okada; Makoto Hanaya, both of Yokkaichi; Akitaka Hattori, Inabe-gun; Takanori Miyake, Yokkaichi; Nobuo Nagira, Yamaguchi; Shunya Ikumi, Yamaguchi; Takashi Hori, Yamaguchi; Norimasa Mizui, Tokuyama, all of Japan

[73] Assignee: Tosoh Corporation, Japan

[21] Appl. No.: 09/188,341

[22] Filed: Nov. 9, 1998

Related U.S. Application Data

[62] Division of application No. 08/760,436, Dec. 4, 1996, Pat. No. 5,883,290.

[30] Foreign Application Priority Data

Dec. 4, 1995 [JP] Japan ................................. 7-315255
Dec. 21, 1995 [JP] Japan ................................. 7-333140
Feb. 9, 1996 [JP] Japan ................................. 8-24086
Apr. 26, 1996 [JP] Japan ................................. 8-107642
Apr. 26, 1996 [JP] Japan ................................. 8-107643
Jul. 24, 1996 [JP] Japan ................................. 8-194808

[51] Int. Cl.[7] ................................. C07C 205/00
[52] U.S. Cl. ................................. 568/705; 560/231
[58] Field of Search ................................. 560/231, 254; 568/705

[56] References Cited

FOREIGN PATENT DOCUMENTS 0 110 629  6/1984  European Pat. Off. .
0 230 286  7/1987  European Pat. Off. .
52-151 135  12/1977  Japan .
52-151 136  12/1977  Japan .
63-174 950  1/1987  Japan .

OTHER PUBLICATIONS

Database WPI Week 7805 Derwent AN 78–09158.
Database WPI Week 7805 Derwent AN 78–09157.
Database WPI Week 8834 Derwent AN 88–240139.
Database WPI Section CH, Week 8443 Derwent AN 84–268751.

*Primary Examiner*—Gary Geist
*Assistant Examiner*—Robert W. Deemie
*Attorney, Agent, or Firm*—Nixon & Vanderhye

[57] ABSTRACT

Benzyl alcohol of high purity is produced by supplying benzyl acetate, water and acetic acid to a hydrolysis reactor packed with a solid acid catalyst. The liquid reaction mixture produced, which contains benzyl acetate, water, benzyl alcohol and acetic acid, is supplied to an acetic acid-water recovery column, Benzyl alcohol and benzyl acetate are recovered while acetic acid is removed and returned to the hydrolysis reactor.

14 Claims, 9 Drawing Sheets

PROCESS FOR PRODUCING BENZYL ACETATE AND BENZYL ALCOHOL

This is a division of application Ser. No. 08/760,436, filed Dec. 4, 1996, now U.S. Pat. No. 5,883,290.

BACKGROUND OF THE INVENTION

1. Field of the Invention

The present invention relates to a process for producing benzyl acetate and benzyl alcohol.

Benzyl acetate itself is useful as a solvent and a perfume. Benzyl alcohol which is derived from the benzyl acetate by hydrolysis or by transesterification with methanol is an important compound useful as a powerful solvent, a non-toxic medical additive, and an intermediate compound for agricultural chemicals and medicines.

2. Description of the Related Art

For industrial production of benzyl acetate, a process is known in which benzyl chloride produced by chlorination of toluene is hydrolyzed by alkali, and the resulting benzyl alcohol is esterified with acetic acid. This process comprises multistage reactions, and includes many steps of separation and purification after the respective reactions. Therefore, the process is complex and is not advantageous economically. Moreover, in the hydrolysis reaction of the second step, an alkali such as sodium hydroxide is required in an equivalent amount or more, and a large amount of a salt containing organic compounds is formed as the by-product, which involves problems in after-treatment thereof.

In a process not industrially conducted, benzyl acetate is produced by reaction of toluene, acetic acid, and oxygen in the presence of a catalyst for oxyacetoxylation. This process produces benzyl acetate in one step reaction without formation of a by-product salt, so that it is advantageous economically and can be of low environmental load.

Many techniques of benzyl acetate production have been disclosed, for example, in JP-B-42-13081, JP-A-52-151135, JP-A-52-151136, JP-B-50-28947, JP-B-52-16101, and JP-A-63-174950 (The term "JP-A" herein means an "unexamined published Japanese patent application", and the term "JP-B" herein means an "examined Japanese patent publication"). However, in these techniques, detailed studies are not made on industrial production process including separation and purification of benzyl acetate. Therefore, known techniques are not satisfactory for production of high-purity benzyl acetate.

On the other hand, benzyl alcohol can be produced by the known processes below. Of these, the processes (1) and (3) are practiced industrially:

(1) Hydrolysis of benzyl chloride by sodium hydroxide,
(2) Hydrolysis of benzyl acetate in the presence of a catalyst, and
(3) Reduction of benzaldehyde by hydrogen in the presence of a catalyst.

The above processes (1) and (2) both produces benzyl alcohol by hydrolysis. The process (1) consumes an equivalent amount or more of sodium hydroxide for stoichiometric reaction of benzyl chloride, involving a problem of after-treatment of a large amount of an aqueous solution of organic compound-containing sodium chloride formed as a by-product. The process (3) employs relatively expensive benzaldehyde as the starting material, and is disadvantageous economically.

The process (2) of hydrolysis of benzyl acetate to produce benzyl alcohol forms useful acetic acid as the by-product without discharging waste water, thus being economical and of low environmental load.

Regarding this hydrolysis process, a method is disclosed in which a mixture of water and benzyl acetate in a volume ratio of water/benzyl acetate of 25 is hydrolyzed at a temperature of 20–30° C. in the presence of Amberlite IR-100, a sulfonic acid type cation-exchange resin (*J. Chem. Soc.*, No.5, 1952, 1607). However, in this process, the catalyst activity is low, and an extremely large amount of water is required, so that the starting material concentration is lowered. Therefore, this process is not industrially advantageous in consideration of the energy for removal of unreacted water from the liquid reaction mixture. Further, the above disclosure does not specifically disclose the method for isolation and purification of the resulting benzyl alcohol.

In another process (Russian Patent: SU1077875), benzyl alcohol of high purity (98%) is obtained at an improved yield by hydrolysis of benzyl acetate in a flow system at a temperature of 90–98° C. at water/benzyl acetate ratio of 3 (by weight) through a porous sulfonic acid type cation-exchange resin containing 2.2–4.0 m-equivalent/g of nitro group by replacing acetic acid with water during the reaction. However, this process, which requires use of a special nitro group-containing resin as the catalyst, is not practical as an industrial process in view of the catalyst cost.

As discussed above, the benzyl alcohol production process has not yet been investigated sufficiently for industrialization including the separation and purification steps, and no process is satisfactory as the process for producing high-purity benzyl alcohol.

SUMMARY OF THE INVENTION

An object of the present invention is to provide a process for economical production of benzyl acetate of high purity.

Another object of the present invention is to provide a process for economical production of benzyl alcohol of high purity.

As the result of comprehensive investigations to solve the above-described problems, this inventor of the present invention found that benzyl acetate of high purity can be produced economically in one step reaction of oxyacetoxylation by constructing a distillation purification process in consideration of the boiling points, the solubilities, and the azeotropy of the components including benzyl acetate as an oxyacetoxylation product, unreacted toluene and acetic acid, and recycling the process distillation fractions to the specified process, by use of a specific catalyst composed of an alloy of palladium and bismuth supported on silica exhibiting high selectivity and has a long life of the catalyst.

The inventors of the present invention found also that benzyl alcohol, which cannot readily be isolated and purified from the hydrolysis product of benzyl acetate can be produced economically by constructing an isolation-purification process in consideration of the azeotropy of the components including benzyl alcohol and acetic acid as hydrolysis products, unreacted benzyl acetate and water, and recycling the process fractions to the specified process, and by using, as the catalyst, a sulfonated styrene-divinylbenzene copolymer having divinylbenzene units in a specified content range, and by reacting the starting materials in a specific ratio.

The inventors of the present invention further found that benzyl alcohol can be produced economically by transesterification of benzyl acetate with methanol in the presence of a basic catalyst, and combining process fractions reasonably in consideration of the later isolation-purification process.

DETAILED DESCRIPTION OF THE PREFERRED EMBODIMENT

Figure 1:
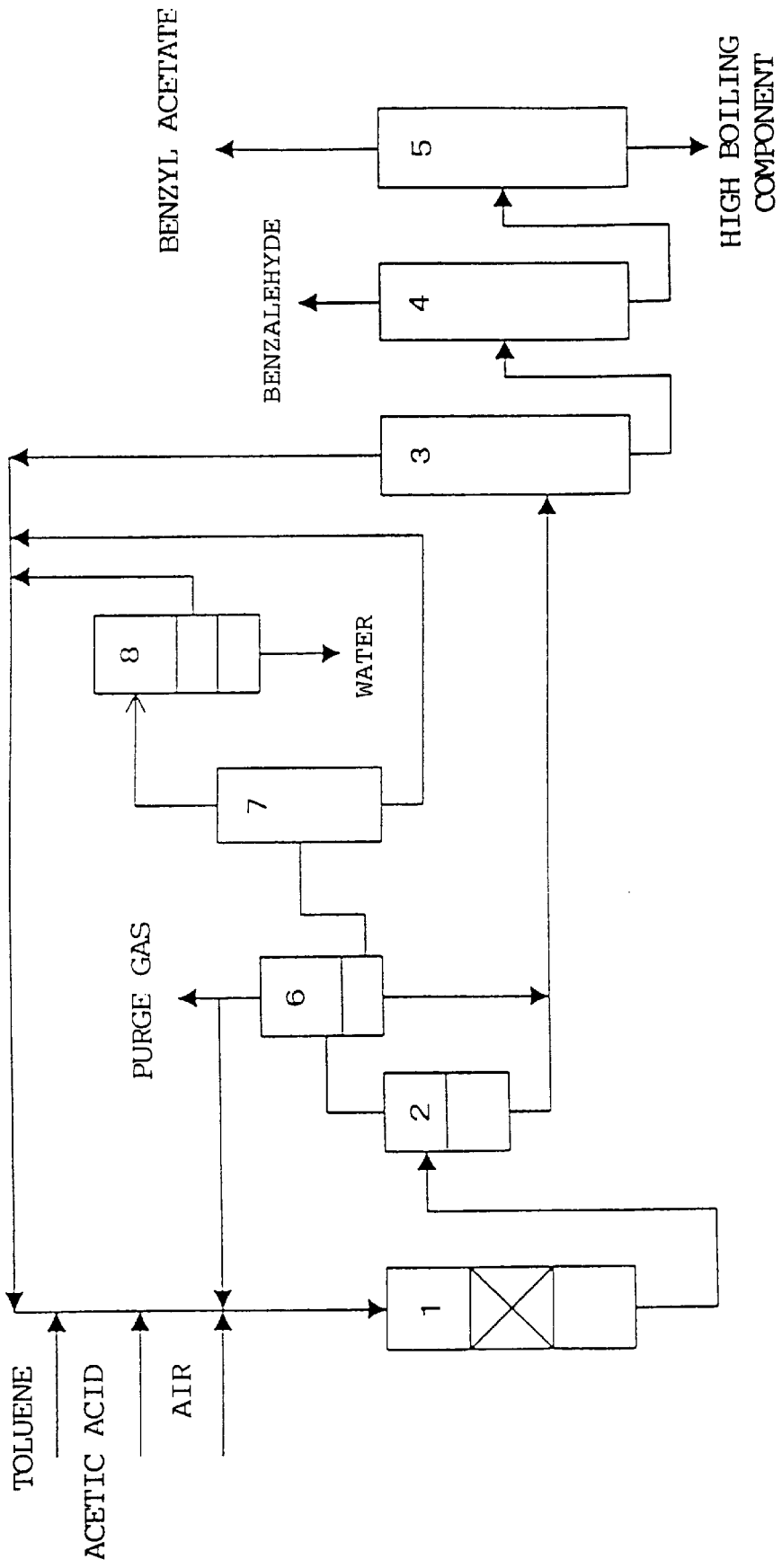
FIG. 1 is a flow sheet showing specifically an example of a process of production of benzyl acetate of the present invention.

Firstly, the process for production of benzyl acetate of the present invention is described.

Toluene and acetic acid are employed as the starting materials in the process of the present invention.

The toluene and the acetic acid employed as the starting materials are not limited in the production processes thereof. For example, the toluene may be a product separated from petroleum distillate, or from cracked oil derived by cracking of petroleum distillate. The acetic acid may be a product obtained by oxidation of acetaldehyde, by oxidation of a hydrocarbon, or by synthesis from methanol and carbon monoxide.

In the process of the present invention, benzyl acetate is produced by oxyacetoxylation by use of toluene, acetic acid, and oxygen in a oxyacetoxylation reactor containing an oxyacetoxylation catalyst.

The oxyacetoxylation catalyst is not specially limited provided that it is capable of causing the intended oxyacetoxylation. For example, the catalysts are preferred which contain palladium having an oxyacetoxylation activity as the main component. Specifically, JP-B-42-13081 discloses a catalyst system comprising palladium supported by alumina and an alkali metal acetate. JP-A-52-151135 and JP-A-151136 disclose catalysts composed of a combination of one of bismuth, molybdenum, manganese, vanadium, and tungsten with palladium supported on silica. JP-B-50-28947 discloses a catalyst system comprising a catalyst composed of a combination of one of bismuth, cobalt, and iron with palladium supported on silica, and potassium acetate. JP-B-52-16101 discloses a catalyst system comprising a catalyst composed of palladium, bismuth, and chromium supported on silica, and an alkali metal acetate. JP-A-63-174950 discloses a catalyst system composed of palladium, and bismuth or lead supported on silica, and a bismuth compound or a lead compound soluble in the reaction system. In the present invention, any of the above catalysts can be used without difficulty. As the catalyst containing oxyacetoxylation-active palladium as a main component, another catalyst described later is useful which comprises an alloy composed of palladium and bismuth supported on silica at a palladium/bismuth ratio ranging from 2.5 to 3.5 (atomic ratio).

Such a catalyst is used as a fixed bed, a suspension catalyst bed and so on, in a reactor, a fixed bed is preferable. The amount of the catalyst depends on its activity, and is not generally specified. However, it corresponds preferably to the total feed of toluene and acetic acid per unit catalyst volume per unit time (LHSV) in the range of from 0.1 to 30 $h^{-1}$ in consideration of production cost. The material of the reactor is not specially limited provided that it is sufficiently corrosion-resistant. For example, when stainless steel is used, SUS316 of JIS or higher corrosion-resistant grade of steel is preferred in consideration of the production cost.

For the oxyacetoxylation, a continuous fixed-bed flow reaction system is preferred in which the liquid starting materials of toluene and acetic acid and a prescribed concentration of oxygen are continuously fed in the reactor, and brought into contact with the fixed catalyst bed. The oxyacetoxylation reactor may be of a single-tubular type or a multi-tubular type, but is not limited thereto. The reaction proceeds by oxidation with generation of heat. The heat control method is not specially limited, and the reaction may be conducted with an adiabatic reaction system, with a multi-tubular reactor system with removal of the reaction heat, or with fractional material feed system.

The composition of the starting material liquid is generally in the range of from 0.1 to 10 moles of acetic acid per mole of toluene. However, when the catalyst employed comprises an alloy composed of palladium and bismuth supported on silica at a palladium/bismuth ratio ranging from 2.5 to 3.5 (atom ratio) as described later, the ratio of acetic acid is generally in the range of from 0.1 to 100, preferably from 0.2 to 40 moles per mole of toluene as mentioned later.

The oxidant employed in the present invention is molecular oxygen. The oxygen may be diluted with an inert gas such as nitrogen. In the practical process, air is preferably used.

The optimum feed rate of oxygen depends on the reaction conditions, the amount of the catalyst, and so forth, and is not generally limited. However, the feed should be controlled to give the total concentration of toluene, acetic acid and benzyl acetate outside the explosion range at least at the outlet portion of the oxyacetoxylation reactor. The feed rate of oxygen per unit catalyst volume per unit time (GHSV) is preferably not more than 5000 $h^{-1}$ in terms of the volume at 0° C. at 1 atmosphere.

The reaction according to the present invention is conducted usually under heated and pressurized conditions. The reaction temperature is preferably in the range of from 80 to 230° C., more preferably from 120 to 200° C. At a higher temperature, side reactions are promoted without advantage, whereas at a lower temperature, the reaction rate is low disadvantageously. The pressure is applied to maintain a liquid phase on the surface of the catalyst, and is generally in the range of from 3 to 100 kg/cm$^2$G, preferably from 5 to 50 kg/cm$^2$G. The reaction time is preferably in the range of from 0.03 to 10 hours as the liquid residence time in the reactor.

The effluent from the oxyacetoxylation reactor is introduced to a gas-liquid separator to separate the liquid phase and the gas phase.

By selecting the method of discharging the effluent from the outlet of the oxyacetoxylation reactor, the gas and the liquid can be separated without an extra independent gas-liquid separator. This reactor is regarded as an integrated reactor-separator, and may be employed in the present invention.

The liquid phase from the gas-liquid separator is a liquid mixture mainly composed of toluene, acetic acid, and benzyl acetate, and is introduced to a starting-material recovery column. In the starting-material recovery column, the liquid is subjected to distillation to recover a liquid mixture distillate composed mainly of unreacted toluene and unreacted acetic acid from the column top, and to obtain a liquid mixture mainly composed of benzyl acetate, the objective product, from the column bottom. The column top distillate, which is recovered from the starting-material recovery column and composed mainly of toluene and acetic acid, is recycled to the oxyacetoxylation reactor.

The bottom liquid recovered from the starting-material recovery column, with or without adjustment of the temperature and pressure, is fed to a low-boiler removal column. In the low-boiler removal column, distillation is conducted to separate a column top liquid mainly composed of benzaldehyde and a bottom liquid mainly composed of benzyl acetate. The distillation conditions for the low-boiler removal column is not specially limited, provided that components such as benzaldehyde having a lower boiling point than benzyl acetate can be removed from the column top.

The bottom liquid mainly composed of benzyl acetate recovered from the low-boiler removal column is, with or without adjustment of the temperature and pressure, introduced to a high-boiler removal column. In the high-boiler removal column, distillation is conducted to obtain benzyl acetate of acceptable product purity from the top of the column, and components such as benzoic acid and benzyl benzoate having a higher boiling point than benzyl acetate is removed from the bottom of the high-boiler removal column. The distillation conditions for the high-boiler removal column is not specially limited, and is selected depending on the required purity of the produced benzyl acetate. For higher quality of benzyl acetate, an additional distillation column may be employed for further distillation and purification.

The embodiments of the present invention are described more specifically by reference to drawings. The present invention includes various types of embodiments, and is not limited to the embodiment shown by the drawings.

In FIG. 1, an oxyacetoxylation reactor 1 is fed with toluene, acetic acid, and air as the starting materials, a recycled liquid phase portion mainly composed of toluene and acetic acid introduced from a starting-material recovery column 3 and a water removal column 7, and a recycled gas phase portion mainly composed of oxygen and nitrogen introduced at least from a condenser 6.

The manner of feeding the starting materials is not specially limited provided that the starting material liquid covers the surface of the catalyst to conduct the reaction in a liquid phase. The starting materials may be fed either in a gas-liquid concurrent system or in a gas-liquid countercurrent system of whether up stream or down stream. The starting liquid materials and/or air may be fed fractionally to the oxyacetoxylation reactor 1.

The gas-liquid mixed phase effluent from the oxyacetoxylation reactor 1 is fed to a gas-liquid separator 2.

The gas phase portion discharged from the gas-liquid separator 2 is introduced to a condenser 6 to separate the liquid phase mainly composed of toluene, acetic acid, and benzyl acetate from the gas phase mainly composed of oxygen and nitrogen.

At least a part of the liquid phase portion separated by the condenser 6 is mixed with the liquid portion from the gas-liquid separator 2, and the mixture is introduced to the starting-material recovery column 3, and the remainder of the liquid phase portion is fed to the water removal column 7. At least a part of the gas phase portion separated by the condenser 6 is recycled to the oxyacetoxylation reactor 1, and the remainder of the gas phase is purged to the outside of the system. The amount of the recycling part of the gas phase portion introduced to the oxyacetoxylation reactor 1 is controlled to give a desired oxygen concentration in the mixture with the fresh air introduced to the reactor 1.

Various condensing apparatuses and operation methods therefor are known, and are applicable to the process of the present invention. The condensation may be conducted in plural times. For example, a condensate containing a larger amount of high-boiling benzaldehyde and benzyl acetate is separated by a first condensation; the separated condensate is fed to the starting-material recovery column 3; the remaining gas phase portion is subjected to a second condensation to remove a condensate composed mainly of toluene, acetic acid, and water; and the condensate is fed to the water removal column 7.

By this method, the load to the starting-material recovery column 3 is reduced; the recycling amount of benzyl acetate to the oxyacetoxylation reactor 1 is reduced to improve the reaction yield of the intended benzyl acetate; and further, the recycling amount of by-product benzaldehyde to the oxyacetoxylation reactor 1 is reduced, advantageously.

Most of the liquid phase portion introduced from the condenser 6 to the water removal column 7 is composed mainly of toluene, acetic acid, and water, and is subjected to distillation in the water removal column 7 to obtain a column top distillate mainly composed of toluene and water as the main distillate fraction. This column top distillate mainly composed of toluene and water is separated into two liquid phases in a settling vessel 8, and the upper phase mainly composed of toluene is recycled without treatment to the oxyacetoxylation reactor 1, and the lower phase mainly composed of water is eliminated. From the bottom of the water removal column 7, acetic acid is obtained, which is recycled without treatment to the oxyace-oxylation reactor 1.

The liquid phase portion from the gas-liquid separator 2 is mixed with a part or the whole of the liquid phase separated by the condenser 6, and the mixture is introduced to the starting-material recovery column 3. This liquid mixture contains a non-condensable gas component such as oxygen and nitrogen dissolved therein, so that the dissolved non-condensable gas is preferably eliminated prior to introduction to the starting-material recovery column 3 by a known apparatus and operation such is a flash evaporator and a vacuum deaerator. This method enables miniaturization of the starting-material recovery column 3, and makes unnecessary an extra device and operation for reducing the loss of useful component by discharge of the non-condensable gas.

The column top distillate of the starting-material recovery column 3, which is mainly composed of toluene and acetic acid is recycled without treatment to the oxyacetoxylation reactor 1.

In the process of the present invention, the recycled liquid phase portion mainly composed of toluene and acetic acid introduced to the oxyacetoxylation reactor 1 contains a small amount of water. A high concentration of water therein can adversely affect the activity and selectivity of the catalyst. Therefore, in order to prevent increase of the water concentration, the gas-liquid separation conditions in the gas-liquid separator 2, the condensation conditions in the condenser 6, and the distillation conditions in the starting-material recovery column 3 and the water removal column 7 are preferably controlled such that the water concentration is kept to be not more than 5% by weight in the entire liquid mixture of the toluene and the acetic acid supplied to the oxyacetoxylation reactor 1 and the recycled liquid phase portion mainly composed of toluene and acetic acid.

As described above, according to the present invention, benzyl acetate of high purity can be produced at a low cost through one step of oxyacetoxylation reaction of toluene, acetic acid, and oxygen and separation from the resulting mixture of the reaction products including benzyl acetate and water and unreacted materials including toluene and acetic acid.

The efficient combination of the gas-liquid separation operation and the condensation operation facilitates recovery and purification of the unreacted materials contained in the gas-liquid mixture effluent from the reactor, reduces the load to the starting-material recovery column, reduces the equipment cost, and saves energy, which is greatly advantageous economically and industrially.

The specific catalyst employed in the present invention is described below.

In the present invention, benzyl acetate is produced by reaction of toluene, acetic acid, and molecular oxygen in a liquid phase in the presence of a catalyst constituted of an alloy supported on silica, the alloy comprising palladium and bismuth in a palladium/bismuth ratio in the range of from 2.5 to 3.5 (atomic ratio).

The silica for the catalyst in the present invention is not specially limited, and may be any silica regardless of the raw material and production process therefor. However, the silica has preferably properties of the BET specific surface area of not less than 10 m$^2$/g, and the pore volume of not less than 0.2 cc/g.

The shape of the catalyst is not limited specially, and may be in a form of a powder, tablet or sphere shape. For a suspension catalyst bed, the catalyst is preferably powdery or granular, and for a fixed catalyst bed, the catalyst is preferably in a form of a molded article such as tablets, sphere shape and extrusion molded articles of a column shape.

The raw materials for palladium and bismuth for preparation of the catalyst employed in the present invention is not specially limited provided that the palladium and the bismuth can finally be alloyed.

Specifically, the raw material for the palladium includes metallic palladium, ammonium hexachloropalladate, potassium hexachloropalladate, ammonium tetrachloropalladate, potassium tetrachlcropalladate, sodium tetrachloropalladate, potassium tetrabromopalladate, palladium oxide, palladium chloride, palladium bromide, palladium iodide, palladium nitrate, palladium sulfate, palladium acetate, potassium dinitrosulfitepalladate, chlorocarbonylpalladium, dinitrodiamminepalladium, tetraamminepalladium chloride, tetraamminepalladium nitrate, cis-dichlorodiamminepalladium, trans-dichlorodiamminepalladium, dichloro(ethylenediamine) palladium, potassium tetracyanopalladate, and the like. The raw material for the bismuth includes metallic bismuth, bismuth chloride, bismuth nitrate, bismuth oxychloride, bismuth acetate, bismuth oxyacetate, bismuth oxide, and the like.

The amount of the supported metal of the catalyst is usually in the range of from 0.1 to 10% by weight based on the total catalyst weight including the supporting silica as an alloy consisting of palladium and bismuth in a palladium/bismuth ratio of from 2.5 to 3.5 (atomic ratio).

The palladium supported by silica should substantially be in a state of an alloy, although excess bismuth may exist in the catalyst without forming the alloy in the present invention.

The palladium substantially in a state of a palladium-bismuth alloy can be confirmed by measuring adsorption of carbon monoxide onto the catalyst, because the palladium-bismuth alloy does not adsorb carbon monoxide. Thus, palladium in a non-alloy state adsorbs carbon monoxide, and can be readily distinguished from the alloy.

The palladium-bismuth alloy of a palladium/bismuth ratio ranging from 2.5 to 3.5 (atomic ratio) shows a characteristic X ray diffraction pattern at 2θ ranging from 30 to 80° as shown in Table 1.

This alloy will not change its X-ray diffraction pattern even when it is heated to 400° C. in a nitrogen atmosphere, or to 200° C. in the air. If the particle size of the alloy is too small for peak assignment in the X-ray diffraction pattern, the applicability of the catalyst to the process of the present invention car be confirmed by analysis by combination of high-resolution electron microscopy with electron beam diffraction or characteristic X-ray fluorescence.

In preparation of the catalyst constituted of the alloy supported on silica, the palladium-bismuth alloy of palladium/bismuth ratio of 2.5–3.5 (atomic ratio) of the present invention, the starting material for the palladium and the bismuth may be deposited by any known method in which palladium and bismuth form the alloy. Specifically the method includes precipitation, ion-exchange, immersion, deposition, blending, and so forth.

In catalyst preparation by immersion, the method of impregnation is not specially limited provided that the palladium and the bismuth finally form an alloy. A palladium material and a bismuth material may be impregnated simultaneously, or successively. For forming a more uniform alloy, the simultaneous impregnation is preferred. In a specific example of the simplest preparation method of the catalyst of the present invention, materials for the palladium and the bismuth are dissolved in a suitable solvent (the starting material salts for palladium and bismuth being preferably mixed in a palladium/bismuth ratio ranging from 2.5 to 3.5 (atomic ratio)); the solution is mixed with silica;

the mixture is kept standing for a prescribed time as necessary, and is dried; and the resulting catalyst precursor is reduced in a hydrogen atmosphere or a hydrogen-containing inert gas atmosphere. Before the reduction treatment with hydrogen, the catalyst precursor may be calcined in an oxygen atmosphere.

The reduction treatment is conducted at a temperature ranging usually from 100 to 700° C., preferably from 200 to 500° C. The reducing agent for the reduction treatment includes gases such as hydrogen, carbon monoxide, and ethylene, alcohols, and hydrazine hydrate. The reduction treatment may be conducted in a gas phase or in a liquid phase.

The calcination before the reduction treatment, if necessary, is conducted in an oxygen atmosphere, in an atmosphere of oxygen diluted with nitrogen, helium, argon or the like, or in the air at a temperature ranging usually from 200 to 700° C.

The toluene and acetic acid used as the starting materials in the present invention are rot limited in their production process. For example, the toluene may be a product separated from petroleum distillate, or from cracked oil derived by cracking of petroleum distillate. The acetic acid may be a product produced by oxidation of acetaldehyde, produced by oxidation of a hydrocarbon, separated from a by-product in peracetic acid, or synthesized from methanol and carbon monoxide. The mixing ratio of toluene to acetic acid is selected as desired in the range of from 0.1 to 100 moles, preferably from 0.2 to 40 moles per mole of toluene.

The reaction may be conducted in the present invention by dissolving a soluble bismuth compound in toluene and/or acetic acid. In this case, the amount of the soluble bismuth compound dissolved in toluene and/or acetic acid is preferably in the range shown the equation below:

$$1 \times 10^{-9} \leq \frac{\text{(Weight of Bismuth as Metal)}}{\text{(Weight of Toluene + Acetic Acid)}} \leq 1 \times 10^{-5}$$

The catalyst employed in the present invention is stable in the reaction system. Therefore, the co-existence of the soluble bismuth compound is not essential. The amount of the co-existing soluble bismuth compound is sufficient in the range shown above. The soluble bismuth compound in an amount much larger than that shown above, may deposit in the process of purification of the produced benzyl acetate to clog pipe lines.

The soluble bismuth compound includes bismuth nitrate, bismuth oxide, bismuth oxyacetate, bismuth hydroxide, bismuth chloride, bismuth oxychloride, basic bismuth carbonate, bismuth acetate, bismuth oxalate, and trimethylbismuth, but is not limited thereto.

The reaction is conducted in a liquid phase in the present invention. The method of the reaction is not specially limited provided that the surface of the catalyst is covered with the starting material liquid. The reaction may be conducted by a batch process, a semi-batch process, a continuous process, or may be conducted with a reactor of fixed-bed flow or suspension system. The catalyst of the present invention may be applied to the aforementioned oxyacetoxylation process.

The amount of the catalyst depends on the method of the reaction, and is not defined generally. However, in consideration of the production cost, the amount of the catalyst in a fixed bed process is such that the total feed of toluene and acetic acid per unit volume of the catalyst per unit time (LHSV) in a fixed bed is in the range of preferably from 0.1 to 50 $h^{-1}$, more preferably from 0.1 to 30 $h^{-1}$, and in a suspension bed, the concentration of the catalyst is preferably in the range of from 0.1 to 30% by weight as the starting materials.

The oxygen partial pressure in the gas phase in the reactor is preferably controlled in the range of from 0.1 to 2 $kg/cm^2$ for maintaining the catalyst life by securing activity and selectivity of the catalyst in the present invention from industrial standpoint. At the oxygen partial pressure of lower than 0.1 $kg/cm^2$, the activity is not sufficient industrially, whereas at the partial pressure of higher than 2 $kg/cm^2$, elution of palladium may be promoted to deteriorate remarkably the catalyst activity. The feed rate of oxygen is preferably in the range of from 0.5 to 4.5 moles per hour per one liter of catalyst. Incidentally, the reactor in the present invention means a vessel, a column, or a tube for synthesis of benzyl acetate by reaction of toluene, acetic acid, and oxygen as the starting materials, including specifically reaction vessels having a suspension bed, a catalyst-packed column or multi-tubular reactor having a fixed bed, etc.

The reaction according to the present invention is conducted usually in a heated and pressurized state. The reaction temperature is in the range of usually from 80 to 230° C., preferably from 120 to 200° C. At a higher reaction temperature than that range, side reactions are promoted without advantage, whereas at a lower temperature, reaction rate is lower disadvantageously. The reaction pressure is not limited specially provided that the liquid phase is maintained on the catalyst surface at the reaction temperature, and is in the range usually of from 3 to 100 $kg/cm^2G$, preferably from 4 to 50 $kg/cm^2G$. The reaction pressure higher than that is not necessary, since the intended reaction proceeds satisfactorily in the above pressure range.

The oxidizing agent in the process of the present invention is oxygen. The oxygen may be diluted with an inert gas such as nitrogen, or the oxidizing agent may be air. The optimum feed rate of the oxygen depends on the reaction temperature, the amount of the catalyst, and so forth, and the gas composition is controlled to be outside the explosion range at the outlet portion of the reactor. The feed rate of oxygen per unit catalyst amount per unit time (GHSV) is preferably not higher than 5000 $h^{-1}$ in terms of the rate at 0° C., and 1 atmosphere.

The reaction time depends on the reaction temperature, the reaction pressure, the catalyst amount, and other conditions, and cannot be defined generally. In a batch or semi-batch system with a suspension catalyst bed, the reaction time is not shorter than 0.5 hour, and preferably in the range of from 1 to 10 hours. In a continuous system with a suspension catalyst bed, or in a flow system with a fixed catalyst bed, the residence time is generally in the range of from 0.03 to 10 hours.

As described above, according to the present invention, industrially useful benzyl acetate can be produced by liquid phase reaction of toluene, acetic acid, and molecular oxygen, by employing a catalyst comprising a specific composition of palladium and bismuth supported on silica, with a high catalyst activity, a high selectivity, and long life of the catalyst.

Furthermore, the benzyl acetate synthesis can be continued for a long term with retention of industrially satisfactory activity and selectivity by controlling the oxygen partial pressure in the gas phase to be within the specified range, and by controlling the feed rate of oxygen to the catalyst to be within the specified range.

Next, the process for producing benzyl alcohol by hydrolysis of benzyl acetate according to the present invention is described below. The process of the present invention includes various modifications, and is not limited to the examples of the embodiment shown by the drawings.

Figure 2:
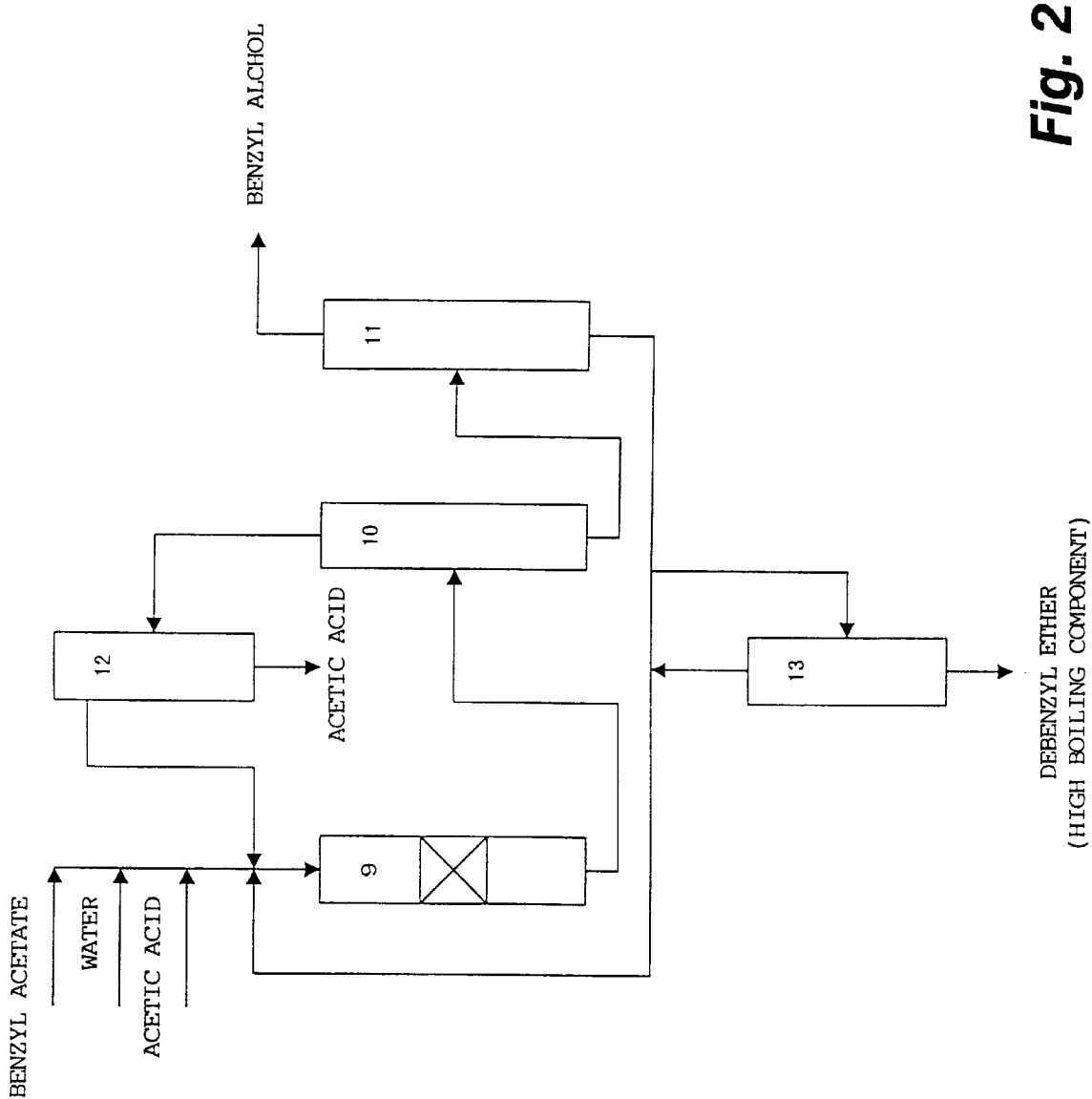
FIG. 2 is a flow sheet showing specifically an example of a process of hydrolysis in the production process of benzyl alcohol of the present invention.

FIG. 2 shows an example a hydrolysis reaction process according to the present invention.

In this process of the present invention, benzyl alcohol is produced by hydrolysis of benzyl acetate by use of a reactor 9 packed with a solid-acid catalyst.

The solid-acid catalyst is not specially limited, and includes inorganic solid-acid catalysts such as silica-alumina, alumina, zirconia, titania, and silica; and organic solid acid-catalyst such as strong acidic cation exchange resin. Of these, preferred are sulfonated styrene-divinylbenzene copolymers as the strongly acidic cation exchange resin.

The sulfonated styrene-divinylbenzene copolymer as the solid-acid catalyst is not specially limited in the divinylbenzene unit content, and usually the content is not higher than 20% by weight. In consideration of the catalyst life and the reaction activity, the divinylbenzene unit content is preferably lower than 8% by weight.

The sulfonated styrene-divinylbenzene copolymer is not specially limited provided that the vinylbenzene unit content is in the aforementioned range, and commercial copolymers are useful. The structure of the copolymer may be either of a gel type or of an MR type (macroreticular type). The gel type copolymer includes simple gel type copolymers and macroporous (MP) copolymers, both being useful. The MR type copolymer is a porous copolymer, and is not limited in the surface area, the porosity, and the average pore diameter. The amount of the acid of the copolymer is not specially limited, but the copolymer has preferably a total ion exchange capacity in the range of from 3.0 to 6.5 m-equivalent/g based on the dry resin.

Benzyl acetate as the starting material is not specially limited, and may be the one produced by oxyacetoxylation reaction from toluene, acetic acid, and oxygen by use of a palladium type catalyst.

As the composition of the starting material, a higher content of benzyl acetate is undesirable since by-products such as dibenzyl ether is increased and the equilibrium conversion and the reaction rate are lower in the higher content of benzyl acetate. On the other hand, at a higher content of water in the liquid mixture of the starting materials, remarkably larger amount of water remains in the reaction mixture after the reaction, which requires a larger amount of energy (latent evaporation heat) for separation and recovery of benzyl acetate from the reaction mixture. Furthermore, at the higher content of water, since the strongly ion-exchange resin is extremely affinitive to water, the fed starting materials tends to form a heterogeneous phase to prevent the adsorption of benzyl acetate onto the catalyst, which lowers the reaction rate and is disadvantageous in industrial production. Therefore, the ratio of water/benzyl acetate is selected usually in the range of from 1/9 to 3/2, preferably from 1/9 to 2/3.

At a higher content of acetic acid in the starting material liquid mixture, the acetic acid content becomes higher to decrease the equilibrium conversion, and the decreased benzyl acetate content reduces he reaction rate, since the hydrolysis reaction of benzyl acetate is an equilibrium reaction and the acetic acid is one of the reaction products. Therefore, the content of acetic acid in the starting material liquid mixture is selected to be not higher than 30% by weight, preferably not higher than 20% by weight.

As mentioned above, the composition of the starting material mixture is important in the present invention. It is particularly preferred to conduct the reaction in a specified three-component system of benzyl acetate/acetic acid/water as shown later.

A useful type of the reactor is a fixed bed continuous reaction system in which the starting materials including benzyl acetate and water, and acetic acid as necessary, are continuously fed. However, the type of the reactor is not limited thereto, and any solid-liquid contact systems may be employed irrespectively of continuous systems or batch systems.

The hydrolysis of benzyl acetate is an equilibrium reaction shown by the reaction equation (1) below.

$$C_6H_5CH_2OCOCH3 + H_2O \rightleftharpoons C_6H_5CH_2OH + CH_3COOH \tag{1}$$

Therefore, the conversion in a single step reaction is limited thermodynamically even if the reaction is conducted in the aforementioned composition range.

More specifically, the equilibrium constant K shown by the equation (2) is 0.40 at 80°C. according to the investigation by the inventors of the present invention. Therefore, with an equimolar material feed composition of benzyl acetate and water (for example, Benzyl acetate/Water/Acetic acid=89.3/10.7/0% by weight), the equilibrium conversion is as low as 38.7%. The conversion of benzyl acetate can be raised by removing at least part of the produced acetic acid in a multi-stage reaction system or reaction distillation system during the reaction.

$$K = [BzOH][AcOH]/[BzOAc][H_2O] \tag{2}$$

where [BzOH] is the concentration of benzyl alcohol, [AcOH] is the concentration of acetic acid, [BzoAc] is the concentration of benzyl acetate, and [H$_2$O] is the concentration of water.

The reaction temperature is selected in the range usually of from 40 to 150° C., preferably from 60 to 120° C. At the reaction temperature of lower than 40° C., the reaction rate is low, whereas at the reaction temperature of higher than 150° C., formation of benzyl ether as the by-product increases to lower the reaction selectivity, and may decompose or deteriorate the catalyst cation-exchange resin.

The reaction pressure is not specifically limited. The pressure may be applied to prevent boiling of the reaction liquid or to prevent significant evolution of bubbles caused by dissolved gas. Usually the pressure is selected in the range of from an atmospheric pressure to 10 kg/cm$^2$G.

The liquid space velocity (LHSV) is selected in the range of usually from 0.1 to 30 h$^{-1}$, preferably from 0.2 to 6 h$^{-1}$.

To the hydrolysis reactor 9, are introduced mixedly the benzyl acetate fed freshly as the starting material, recycled benzyl acetate from an alcohol concentration column 11, and a recycled aqueous acetic acid solution from an acetic acid-water separation column 12. The method of mixing is not specially limited. For example, the mixing is conducted in a mixing vessel provided before the reactor for sufficient agitation and mixing, or by an inactive packed bed provided at the upstream side to the catalyst layer in the reactor.

At the outlet of the hydrolysis reactor 9, the composition of the liquid corresponds preferably at least to 70% equilibrium conversion. At the composition of lower than 70% equilibrium conversion, a larger amount of energy is required for recovery of the unreacted benzyl acetate, which can be disadvantageous in industrial production.

The reaction mixture discharged from the hydrolysis reactor 9, which is composed of benzyl acetate, benzyl alcohol, water, and acetic acid, is introduced to an acetic acid-water recovery column 10. From the top of the acetic acid-water recovery column 10, acetic acid and water is recovered, and is introduced to an acetic acid-water separation column 12. Acetic acid is recovered from the bottom of the acetic acid-water separation column 12, and the fraction mainly composed of water is removed from the top thereof, and is recycled to the hydrolysis reactor 9.

In operation of the acetic acitic water recovery column 10, the concentration of acetic acid is very important since the acetic acid as an extracting agent destroys the azeotrope composed of water and benzyl alcohol to bring benzyl acetate and benzyl alcohol to the column bottom. The concentration of the acetic acid should be controlled to be not less than 10 mol % based on the water. At the acetic acid concentration of lower than 10 mol % relative to water, azeotropes composed of water and benzyl acetate, and of water and benzyl alcohol are formed in the acetic acid-water recovery column 10, thereby benzyl acetate and benzyl alcohol being distilled out from the column top, which may make the intended separation impossible. With the aforementioned material composition, no problem is caused in the operation of the column. However, when the reaction is conducted at a higher concentration of water or at a lower hydrolysis conversion ratio, the acetic acid concentration at the inlet of the acetic acid-water recovery column becomes lower, so that acetic acid should be replenished to increase the acetic acid concentration up to 10 mol % relative to water.

The benzyl alcohol and benzyl acetate discharged from the bottom of the acetic acid-water recovery column 10 is introduced to an alcohol concentration column 11 to obtain an azeotropic mixture composed of benzyl alcohol and benzyl acetate from the column top, and benzyl acetate from the column bottom. The benzyl acetate obtained from the column bottom is recycled to the hydrolysis reactor 9. Since the bottom liquid contains a small amount of high-boiling impurities including dibenzyl ether, a part of the bottom liquid is generally introduced to a heavy separation column 13 to remove high-boiling components mainly composed of dibenzyl ether. Thereby the concentration of impurities is decreased in the recycled benzyl acetate recycled to the hydrolysis reactor 9.

Figure 3:
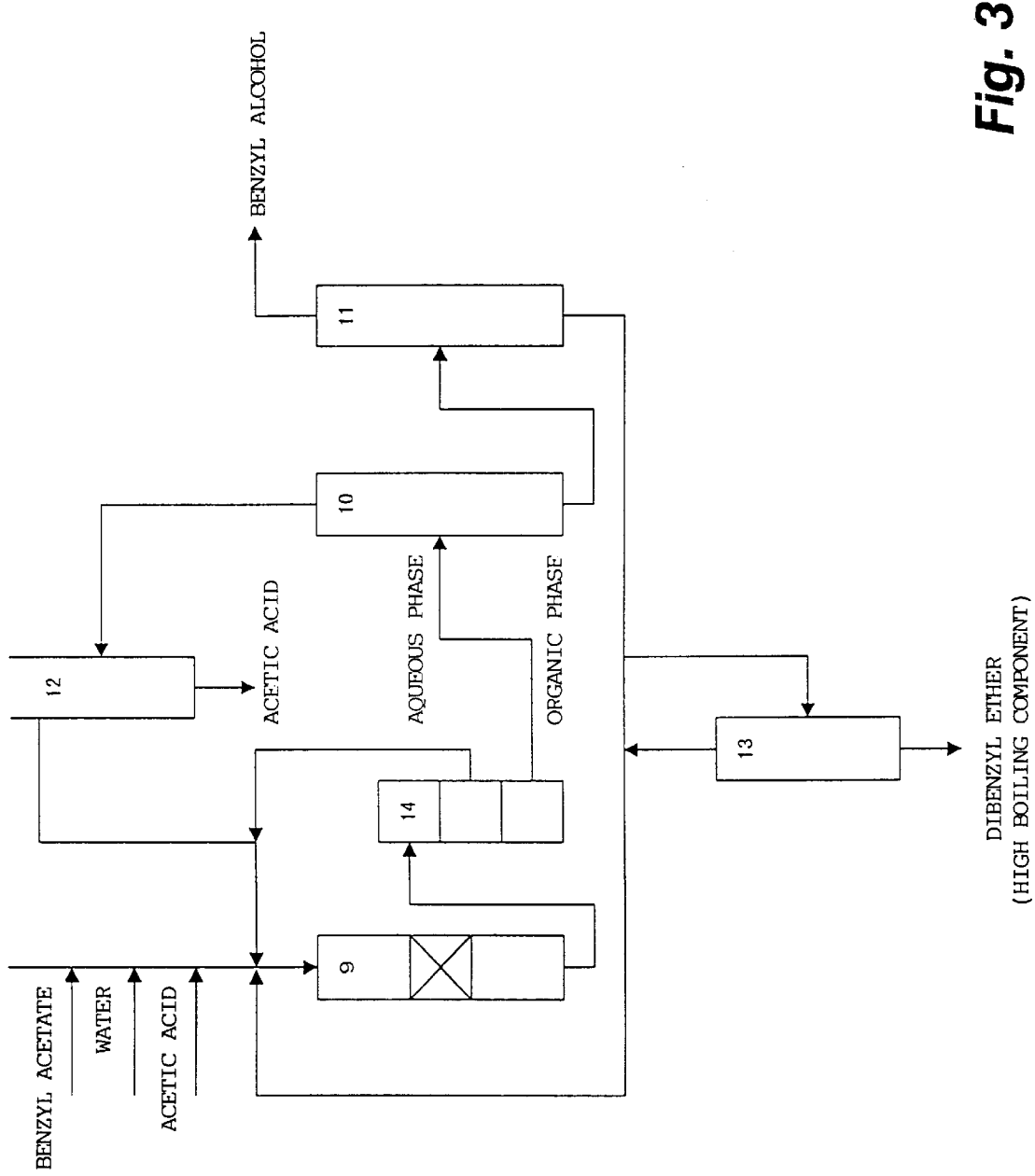
FIG. 3 is a flow sheet showing specifically an example of a process of hydrolysis utilizing liquid-liquid separation in the production process of benzyl alcohol of the present invention.

FIG. 3 shows an example of the hydrolysis reaction process utilizing liquid-liquid separation.

In this process, water is removed from the reaction liquid mixture by utilizing the low solubilities of benzyl alcohol and benzyl acetate in water. The reaction mixture discharged from the hydrolysis reactor 9 is introduced to a liquid-liquid separator 14 to separate it into an aqueous phase and an organic phase. The separated aqueous phase is recycled to the hydrolysis reactor 9, and the separated organic phase is introduced to the acetic acid-water recovery column 10. By this simple operation, water and a part of the acetic acid are removed, and the large energy consumption by the acetic acid-water recovery column is saved, whereby the production cost can be reduced.

The liquid-liquid separation is conducted in principle at a temperature where the liquid-liquid separation occurs. In consideration of partition coefficients of the respective components, separation time, and separation cost, the temperature is preferably in the range of from 10 to 60° C. In the case where the reaction liquid mixture contains an extremely large amount of water or acetic acid, and the liquid-liquid separation does not occur or takes a long time, the process of FIG. 2 in which liquid-liquid separation is not conducted is preferably employed for the production of benzyl alcohol.

In the hydrolysis process shown in FIG. 2 or FIG. 3, benzyl alcohol having a purity of 99% or higher can be obtained from the top of the alcohol concentration column 11 by controlling the operation conditions of the alcohol concentration column 11. Benzyl alcohol of a higher purity containing less benzyl acetate can be obtained by further conducting azeotropic distillation or extractive distillation.

Figure 4:
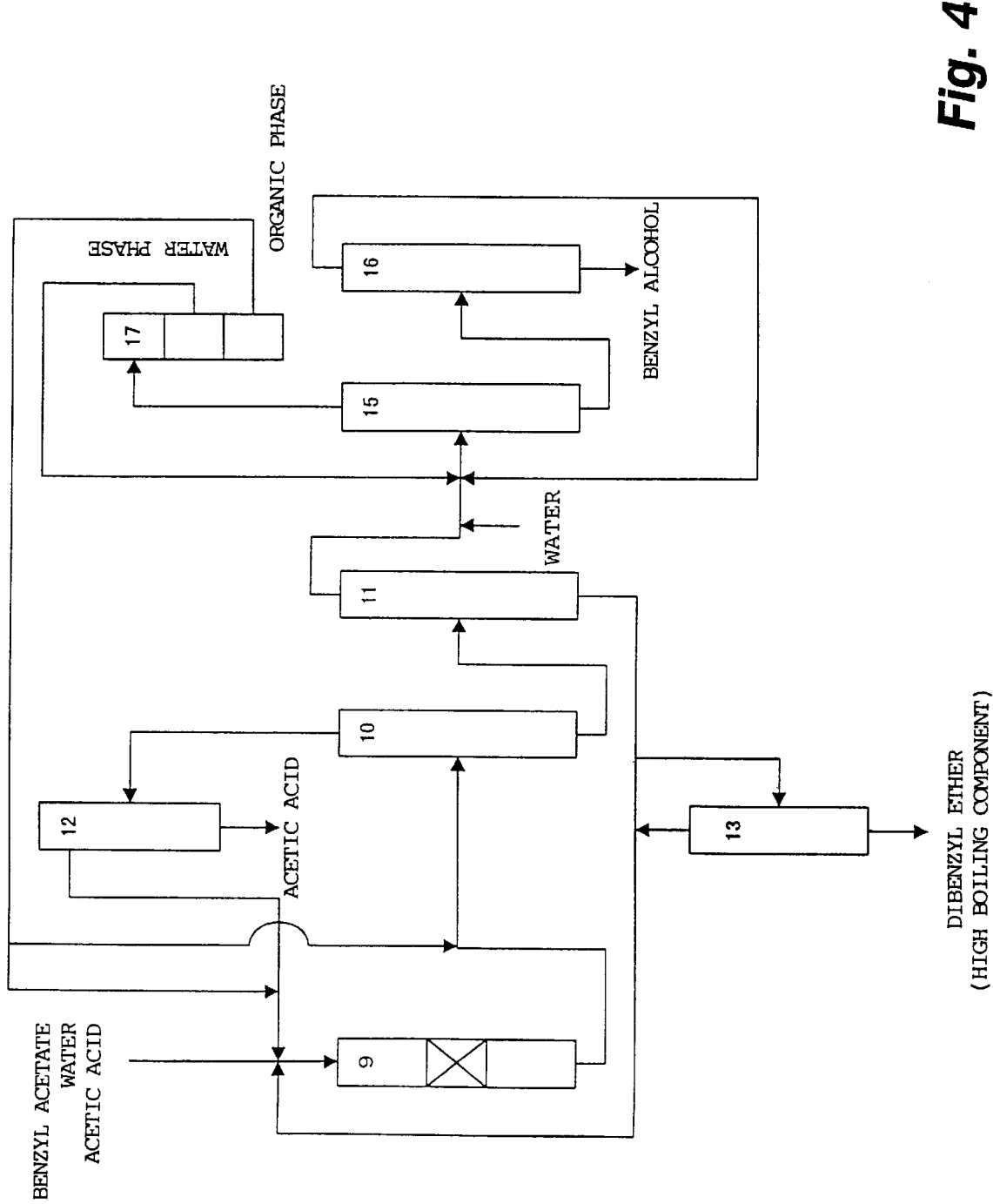
FIG. 4 is a flow sheet showing specifically an example of a process of azeotropic distillation employing water in the production process of benzyl alcohol of the present invention.

FIG. 4 shows an example of the azeotropic distillation employing water.

The column top distillate of the alcohol concentration column 11 is introduced to a first alcohol purification column 15, in which benzyl acetate is separated from benzyl alcohol by utilizing water as the azetrope. The distillate from the column top is introduced to a liquid-liquid separator 17 to separate the two liquid phases. A part of the separated aqueous phase is returned to the first alcohol purification column 15 as the recycle. The organic phase which contains benzyl acetate, benzyl alcohol, and a small amount of water is recycled to the acetic acid-water recovery column 10 or the hydrolysis reactor 9.

The bottom liquid, which contains a small amount of water in addition to benzyl alcohol, of the first alcohol purification column 15 is introduced to a second alcohol purification column 16. In the second alcohol purification column 16, the water in the benzyl alcohol is completely removed from the column top by utilizing azeotrope of benzyl alcohol and water to obtain high purity benzyl alcohol from the column bottom. The column top distillate is recycled to the first alcohol purification column 15. Benzyl alcohol of higher quality can be obtained by distillation and purification by use of another distillation column.

In the above process, benzyl alcohol is purified by means of two purification columns: the first column for separation only of benzyl acetate, and the second column for separation of water. This process is advantageous in comparison with the purification by means of one purification column in points below.

(1) The operation temperature can be lowered, and the first column can be operated at an atmospheric pressure, which reduces the equipment cost.

(2) The lower operation temperature prevents deterioration of the product quality.

(3) A less expensive heating source (low pressure steam) can be used to reduce the energy cost.

(4) The operation of the distillation columns is stabilized more.

Figure 5:
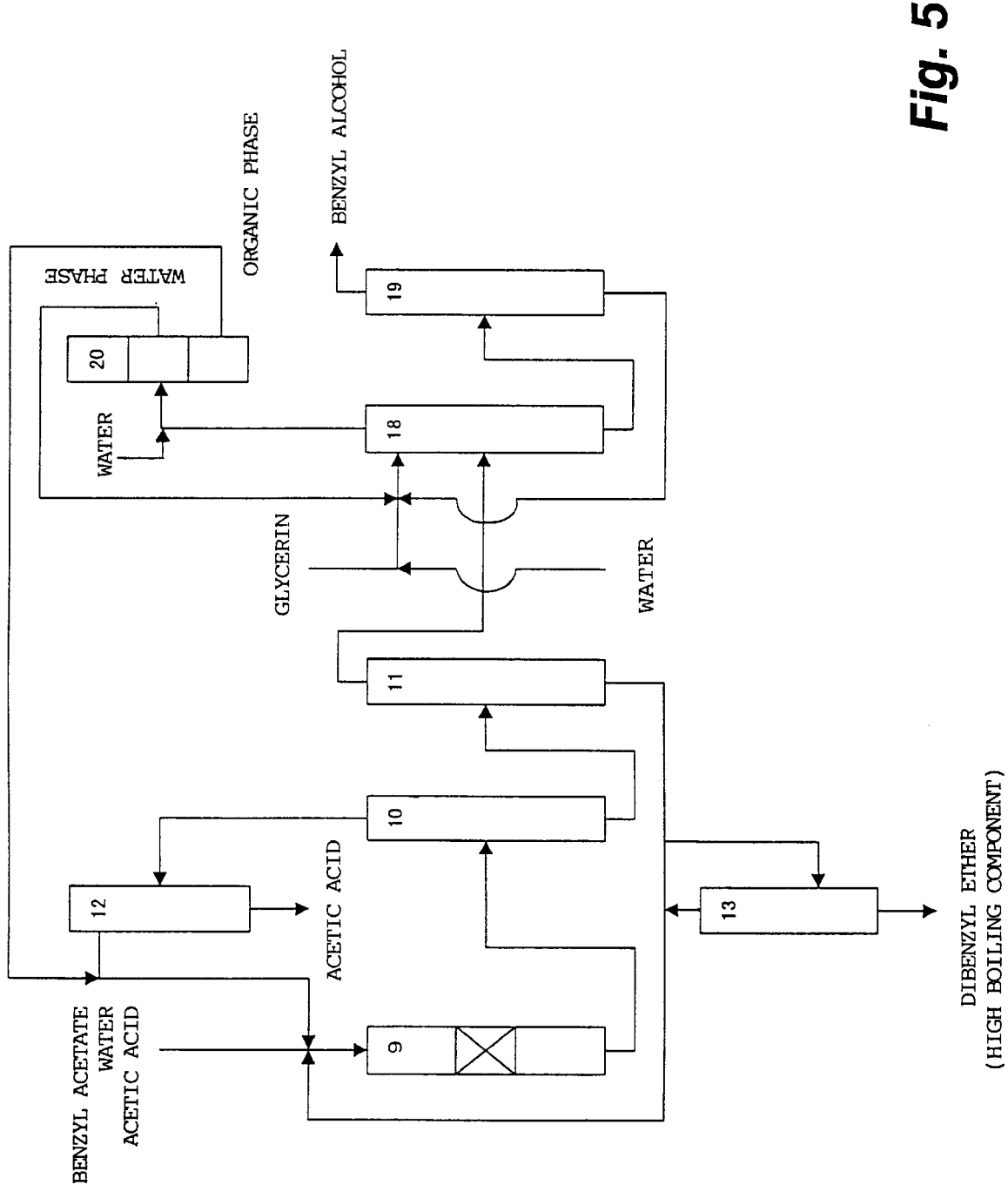
FIG. 5 is a flow sheet showing specifically an example of a process of extractive distillation employing glycerin in the production process of benzyl alcohol of the present invention.

FIG. 5 shows an example of extractive distillation process employing glycerin.

The column top distillate of the alcohol concentration column 11 is introduced to an extractive distillation column 18. In the extractive distillation column 18, glycerin is used as the extracting agent, and the introduced distillation fraction is further separated into a column top distillate composed mainly of benzyl alcohol and benzyl acetate and a column bottom liquid composed of benzyl alcohol and glycerin.

To the distillate from the column top, water is added, and then the distillate is introduced to a liquid-liquid separator 20 to separate into two liquid phases of the two phases, the aqueous layer composed of water and glycerin is recycles to the extractive distillation column 18, and the organic phase is recycled to the hydrolysis reactor 9. Otherwise, the aqueous phase in the liquid-liquid separator 20 may be recycled, after removal of water, to the extractive distillation column 18. The organic phase in the liquid-liquid separator 20, which contains a small amount of glycerin, is recycled to the hydrolysis reactor 9, preferably after removal of glycerin.

The column bottom liquid containing benzyl alcohol and glycerin of the extractive distillation column 18 is introduced to a product column 19, and benzyl alcohol of high purity can be obtained from the top of the column. The column bottom liquid composed mainly of glycerin is recycled to the extractive distillation column 18. Benzyl alcohol of higher quality can be obtained by distillation and purification by use of another distillation column.

In the present invention, the aforementioned columns of the acetic acid-water recovery column 10, the alcohol concentration column 11, the acetic acid-water separation column 12, the heavy separation column 13, the first alcohol purification column 15, the second alcohol purification column 16, the extractive distillation column 18, and the product columns 19 are usual continuous multi-stage distillation columns such as packed columns and plate columns. The liquid-liquid separators 14, 17, 20 are usual settling vessels.

As described above, benzyl acetate and water, and benzyl alcohol and water which are not readily separable owing to the azeotropy can be separated readily by utilizing the acetic acid in the reaction liquid of the hydrolysis reaction as the extracting agent. Thereby, water and acetic acid can be completely separated from the reaction liquid mixture to obtain high-purity benzyl alcohol at remarkably reduced production cost.

The water separated by the acetic acid-water separation column is recycled to the hydrolysis reactor, and the acetic acid is useful as an industrial chemical. Therefore, the process does not discharge waste water and causes less environmental load.

A still higher purity of benzyl alcohol can be produced efficiently by concentrating the benzyl alcohol by the alcohol concentration column, and subsequently subjecting the concentrated benzyl alcohol to azeotropic distillation with water or extractive distillation with glycerin.

The preferred hydrolysis catalyst of the present invention is explained below.

In the hydrolysis reaction of benzyl acetate of the present invention, the preferred catalyst is a sulfonated styrene-vinylbenzene copolymer which is a strongly acidic cation exchange resin.

The sulfonated styrene-vinylbenzene copolymer should contain the divinylbenzene units at a content of less than 8% by weight. The copolymer of the divinylbenzene content of 8% by weight or higher is less reactive and does not achieve the object of the present invention. The content of the divinylbenzene units is preferably not lower than 1% by weight in consideration of the catalyst strength, and is preferably not higher than 7% by weight in consideration of the catalyst life.

The sulfonated styrene-divinylbenzene copolymer employed in the present invention is not specially limited provided that divinylbenzene unit content is in the aforementioned range, and may be a commercial product. The structure may be either of a gel type of a macroreticular type (MR type). The gel type copolymer includes simple gel type copolymers and macroporous (MP) copolymers, both being useful. The MR type copolymer is a porous copolymer, and is not limited in the surface area, the porosity, and the average pore diameter. The total ion exchange capacity is preferably in the range of from 3 to 6.5 m-equivalent/g based on the dry resin.

In the present invention, the hydrolysis reaction is conducted by a continuous fixed bed reaction system in which benzyl acetate and water as the starting materials are fed continuously to a reactor packed with a catalyst composed of the aforementioned sulfonated styrene-vinylbenzene copolymer. The starting materials may further contain, as desired, acetic acid in addition to the benzyl acetate and water to improve mixing of the starting materials. The water and the benzyl acetate are used in a water/benzyl acetate mole ratio ranging usually from 0.5 to 30, preferably from 1 to 15. At the mole ratio of less than 0.5, the conversion of benzyl acetate may be lower, whereas at the mole ratio of higher than 30, the reaction rate may be lower and be disadvantageous in industrial production. The concentration of acetic acid in the entire starting material is controlled to be in the range of usually from 0 to 30% by weight, preferably from 3 to 20% by weight. At the acetic acid concentration of higher than 30% by weight, the amount of acetic acid which is a reaction product is larger and the equilibrium deviates to the starting material side disadvantageously because the hydrolysis reaction of benzyl acetate is an equilibrium reaction.

The reaction temperature is controlled in the range of usually from 40 to 150° C., preferably from 60 to 120° C. At the reaction temperature of lower than 40° C., the reaction rate is lower, whereas at the reaction temperature of 150° C., the by-product dibenzyl ether increases to lower the selectivity, and further the catalyst cation exchange resin may be decomposed or deteriorated. The reaction pressure is not specially limited, and the reaction may be conducted under pressure, as desired. The liquid space velocity (LHSV) is controlled to be in the range of usually from 0.1 to 30 h$^{-1}$, preferably from 0.2 to 6 h$^{-1}$. The reaction mixture discharged from the reactor is subjected to after-treatment according to a conventional process or the aforementioned process to obtain benzyl alcohol.

As described above, benzyl alcohol can be produced efficiently and economically by use of the sulfonated styrene-divinylbenzene copolymer having divinylbenzene unit content in the specified range according to the present invention.

The starting material composition specified for the hydrolysis reaction in the present invention is explained below.

The composition of the starting material liquid is explained by reference to the composition diagram (FIG. 6) for the starting materials of ternary system of benzyl acetate/acetic acid/water. Table 2 shows the starting material compositions at the indicated points in FIG. 6.

Figure 6:
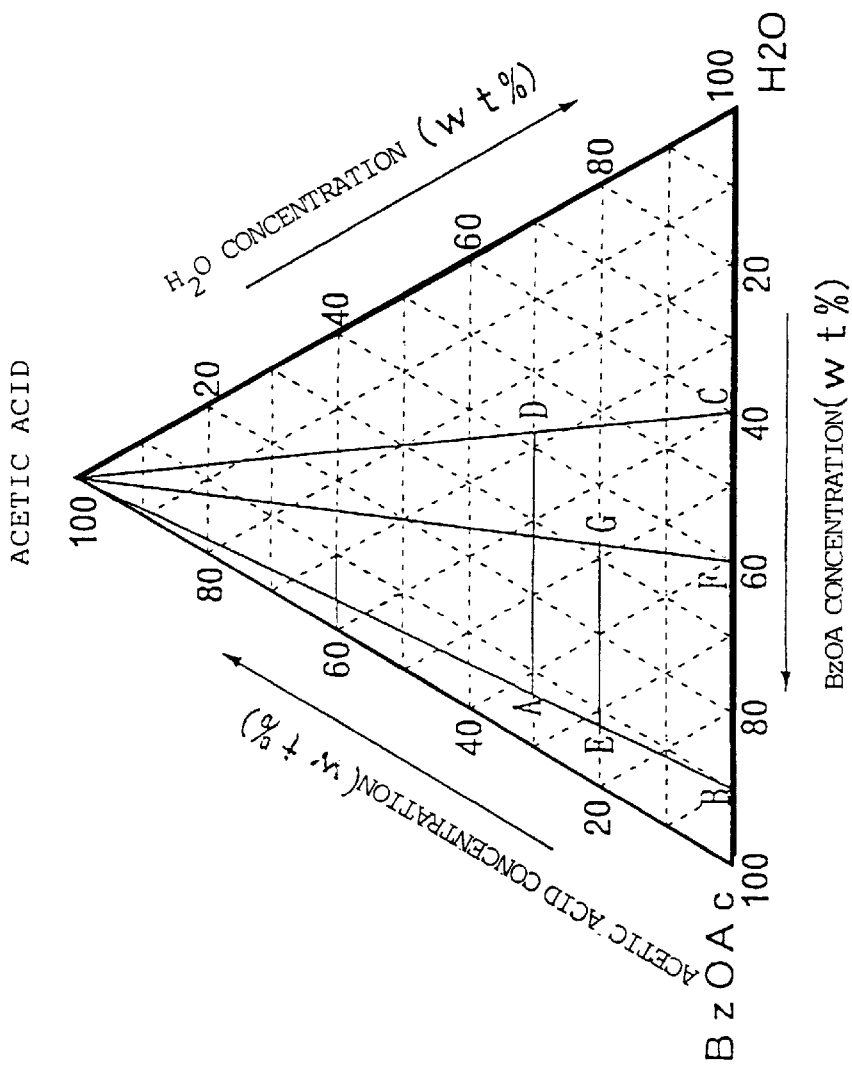
FIG. 6 is a diagram showing compositions of a ternary component system composed of benzyl acetate, acetic acid, and water in the process of production of benzyl alcohol of the present invention.

The composition of the starting material in the present invention should be in the closed region surrounded by the line segments derived by bonding the points A, B, C, and D in FIG. 6. Specifically, when the material contains y % by weight of water, x % by weight of benzyl acetate, and z % by weight of acetic acid (where x+y+z=100), the compositions of the starting materials are in the ranges:

$$1/9 \leq y/x \leq 3/2, \text{ and } 0 \leq z \leq 30$$

At the starting material composition having the acetic acid content higher than the line A-D in FIG. 6 (z>30), the produced acetic acid increases, thereby lowering the equilibrium conversion and lowering the benzyl acetate content to decrease the reaction rate.

At the starting material composition having the benzyl acetate content higher than the line A-B in FIG. 6 (y/x<1/9), by-products such as dibenzyl ether increase, and the equilibrium conversion and the reaction rate become lower undesirably.

At the starting material composition having the water content higher than the line C-D in FIG. 6 (3/2<y/x), a larger amount of water remains after the reaction, and a large amount of energy (latent evaporation heat) is required for separation and recovery of benzyl acetate from the reaction liquid mixture. Moreover, the strongly acidic ion exchange resin generally is extremely affinitive to water, and in the above region, where the supplied starting material becomes heterogeneous, the adsorption of benzyl acetate to the catalyst is prevented to lower the reaction rate disadvantageously in industrial production.

As described above, the starting material composition in the present invention is in the closed region surrounded by the lines bonding the points A, B, C, and D successively. For obtaining a higher purity of benzyl alcohol, the composition is preferably in the closed region surrounded by the lines bonding the points E, B, F, and G successively, namely in the range of $1/9 \leq y/x \leq 2/3$, and $0 \leq z \leq 20$.

A reactor useful in the present invention is a fixed-bed continuous reaction type reactor which is fed continuously with benzyl acetate and water as the starting materials, and acetic acid as necessary, and reacts them. However, the type of the reactor is not limited thereto, but may be any usual method for solid-liquid contact. For improving the conversion of benzyl acetate, a multi-stage reaction type, a reaction distillation type, may be employed in which at least a part of the formed acetic acid is removed during the reaction.

The reaction temperature in the present invention is controlled in the range of usually from 40 to 150° C., preferably from 60 to 120° C. At the reaction temperature of lower than 40° C., the reaction rate is lower, whereas at the reaction temperature of higher than 150° C., the by-product dibenzyl ether produced more to lower the selectivity, and may decompose or deteriorate the catalyst cation exchange resin. The reaction pressure is not specially limited, but is controlled to be at such a pressure that prevents boiling of the reaction liquid or remarkable bubble formation caused by a dissolved gas. The pressure is usually in the range of from an atmospheric pressure to 10 kg/cm$^2$G. The liquid space velocity (LHSV) is controlled to be in the range of usually from 0.1 to 30 h$^{-1}$, preferably from 0.2 to 6 h$^{-1}$.

The reaction mixture discharged form the reactor is subjected to after-treatment by a known process or the aforementioned process to obtain benzyl alcohol.

As described above, according to the present invention, benzyl alcohol can be produced efficiently and economically by hydrolysis reaction of benzyl acetate in the specified range of the starting material composition.

Next, the process for producing benzyl alcohol by transesterification of benzyl acetate with methanol according to the present invention is explained below.

In the method of the present invention, benzyl acetate is fed to the upper portion of a reaction-distillation column, and methanol is fed to the lower portion of the reaction-distillation column, and the benzyl acetate and the methanol are brought into contact countercurrently in the presence of a basic catalyst to cause transesterification to produce benzyl alcohol.

In the reaction, an impurity in the starting material may lower the reaction rate or cause clogging. For example, when sodium methylate is used as the basic catalyst, an acidic substance such as benzoic acid and acetic acid, or water in the starting materials may form sodium benzoate, or sodium acetate as shown by the reaction formulas below.

$$C_6H_5COOH+CH_3ONa \rightarrow C_6H_5COONa+CH_3OH \quad (3)$$

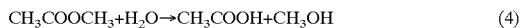
$$CH_3COOCH_3+H_2O \rightarrow CH_3COOH+CH_3OH \quad (4)$$

$$C_6H_5CH_2OCOCH_3+HO \rightarrow CH_3COOH+C_6H_5CH_2OH \quad (5)$$

$$CH_3COOH+CH_3ONa \rightarrow CH_3COONa+CH_3OH \quad (6)$$

Such a sodium salt is nearly insoluble in the benzyl acetate as the starting material and methyl acetate as a by-product of transesterification, may deposit and scale around the benzyl acetate feed plate where the concentrations of benzyl acetate and methyl acetate are high to cause flooding trouble. Furthermore, since these reactions involve the catalyst (sodium methylate), the catalyst itself may be inactivated or consumed to decelerate the reaction. When sodium hydroxide is used as the catalyst, similar reactions occur as those with sodium methylate.

Therefore, the benzyl acetate and methanol as the starting material contain desirably less concentrations of acidic substances such as benzoic acid and acetic acid, and a less concentration of water. The allowable concentrations of such impurities depend on the mole ratio of methanol to benzyl acetate, catalyst concentration, and concentrations of the respective impurities, and is not limited specially. For example, the benzoic acid concentration in benzyl acetate is usually not higher than 0.05% by weight, preferably not higher than 0.03% by weight, still more preferably not higher than 0.02% by weight. The acetic acid concentration in benzyl acetate is usually, not higher then 0.1% by weight, preferably 0.05% by weight, still more preferably not higher than 0.03% by weight. The water concentration in benzyl acetate is usually not higher then 0.05% by weight, preferably 0.03% by weight, still more preferably not higher than 0.02% by weight. The water concentration in methanol is usually not higher than 0.2% by weight, preferably 0.1% by weight, still more preferably not higher than 0.05% by weight.

In a preferred embodiment of the present invention, the benzyl acetate as the starting material is produced by the oxyacetoxylation described before. The methanol is recovered by hydrolysis of methyl acetate formed in the transesterification as the by-product, and distillation by a methanol recovery column. Methanol is also recovered from the bottom of the reaction distillation column by distillation through a methanol separation column. The both kinds of methanol is recycled to the reactor. Therefore, replenishment of methanol is only a small amount corresponding to the operation loss.

The basic catalyst in the present invention includes alkali metal hydroxides such as sodium hydroxide, and potassium hydroxide; and alcoholates such as sodium alcoholate, and potassium alcoholate. These basic catalysts are solid. Therefore the catalyst is fed in a state of a solution in alcohol.

The alcohol used in the transesterification reaction is not limited to methanol. However, methanol is the most suitable in consideration of the solubility of the catalyst, and the separation of the alcohol from water after the hydrolysis of acetate ester formed in the transesterification. Accordingly, as the alcohol for dissolving the catalyst, methanol is the most suitable. Otherwise, the catalyst may be used as a solution in benzyl alcohol.

The required amount of the catalyst depends on the kind of the catalyst, and cannot generally be specified. Although a larger amount of the catalyst is advantageous to raise the reaction rate, it may cause deposition of the salt as described before. The amount of the catalyst should be decided in consideration of the above matters. For example, sodium hydroxide as the catalyst is used in an amount of from 0.01 to 1% by weight, preferably from 0.02 to 0.2% by weight to the starting benzyl acetate. Sodium methylate as the catalyst is used in an amount corresponding to that of sodium hydroxide multiplied by the molecular weight ratio (54/40).

The reaction distillation column may be of a conventional type, such as a packed column and a plate column, and is not specially limited.

The catalyst is fed to the reaction distillation column preferably at the benzyl acetate feed position (feed plate) or a higher position (upper plate).

In the reaction distillation column, preferably, the zone of the column between the methanol feed position and the benzyl acetate feed position is employed as a reaction section; the zone above the benzyl acetate feed position is employed as an enriching section; and the zone below the methanol feed position is employed as a distillation-separation section called a stripping section. The enriching section serves to keep benzyl acetate, a starting material, and benzyl alcohol, the product below the column top. The stripping section serves to keep the produced methyl acetate above the column bottom. Benzyl acetate and benzyl alcohol, which have respectively a boiling point higher sufficiently than the distilling components, namely methyl acetate and methanol, can readily be separated from the distilling components. Therefore, not so many plates are required for the stripping section. The size of the reaction section is decided in consideration of the residence time of benzyl acetate as the starting material, and the theoretical plate number of distillation. The required residence time depends on the gas-liquid contact efficiency in the column, the catalyst concentration, the mole ratio of methanol to benzyl acetate, and the reaction temperature, and is not specially limited. A longer residence time, and a larger theoretical plate number do not retard the reaction, but are not economical. Accordingly, the residence time is preferably in the range of from 1 to 60 minutes, and the total theoretical plate number of the reaction-separation column is preferably in the range of from 3 to 50 plates.

Benzyl alcohol is relatively stable to heat. However, the benzyl alcohol is preferably not brought to high temperature in the presence of the catalyst or the sodium salt. Thus the column bottom temperature of the reaction distillation column is kept preferably at a temperature lower than the normal boiling point of benzyl alcohol by discharging a part of methanol from the bottom.

The operation pressure of the reaction-distillation column is not specially limited. However, in consideration of the vapor pressures of methyl acetate and methanol which are main components at the column top, operation at an atmospheric pressure is most reasonable and economical. The temperature of the respective portions of the column is a function of the operation pressure, the feed mole ratio of benzyl acetate and methanol, the catalyst concentration, the temperature or the composition of the column bottom, the plate numbers of the respective sections, and the reflux ratio.

The feed amount of methanol is equimolar to the starting benzyl acetate or larger. However, with excessively larger amount of methanol, a larger amount of methanol is delivered together with produced methyl acetate to the hydrolysis process, and the increase of the recycled methanol increases energy consumption. Therefore, the feed mole ratio of methanol to the starting benzyl acetate is in the range of usually from 1.1 to 10, preferably from 1.5 to 5.

In the present invention, the mixture obtained from the bottom of the reaction-distillation column and mainly composed of benzyl alcohol and methanol is introduced to a methanol separation column, and is subjected to distillation. The column top distillate mainly composed of methanol is recycled to the reaction-distillation column. In this distillation, when methanol contains a larger amount of water, the distillation is controlled preferably to bring the water into the benzyl alcohol fraction at the column bottom.

The methanol separation column may be of any conventional type.

The operation pressure of the methanol separation column is not specially limited. However, the column is operated preferably under a reduced pressure to keep the benzyl alcohol at or below the normal boiling point as mentioned above.

Benzyl alcohol and methanol can be separated with less number of the plates at lower reflux ratio because of the remarkably high relative volatility thereof. Therefore, as an effective methanol separation process, methanol may be distilled out without consideration of the water-concentration of the distilled methanol; the water-containing methanol is dehumidified through a dehumidification column packed with a water adsorbent such as silica gel, zeolite, and active carbon; and then the dehumidified methanol is recycled to the reaction-distillation column.

The column bottom liquid mainly composed of benzyl alcohol of the methanol separation column is introduced to an alcohol purification column. Before introduction to the alcohol purification column, the column bottom liquid of the methanol separation column is preferably concentrated by a solid separator to remove, from the liquid by deposition, the solid matter such as sodium benzoate, sodium acetate, and catalyst dissolved in the liquid, and the evaporate is introduced to the alcohol purification column. In the alcohol purification column, low-boiling impurities including methanol, water, benzaldehyde, and the like are removed from the column top, the product benzyl alcohol is taken out from the middle portion of the column, and the column bottom liquid is recycled to the solid separator.

The solid separator and the alcohol purification column are operated under a reduced pressure in consideration of the thermal stability of benzyl alcohol. The type of the solid separator is not specially limited, and exemplified by an evaporator equipped with an inside scraper, and a thin film evaporator.

The alcohol separation column may be divided into two columns: an impurity separation column, and an alcohol purification column. In such a two-column alcohol separation system, impurities including methanol, water, and benzaldehyde are removed from the top of the impurity separation column, and the bottom liquid thereof is introduced to the alcohol purification column, where benzyl alcohol as the product is taken out from the top of alcohol purification column, and the bottom liquid is recycled to the solid separator.

The mixture coming out from the top of the reaction-distillation column is mainly composed of methyl acetate and methanol, and is introduced to the middle portion of an extractive distillation column. In the extractive distillation column, distillation is conducted with water fed to the upper portion of the column, and from the top of the column, a mixture composed mainly of methyl acetate and water is taken out. This column top distillate is preferably introduced together with the distillate of the acetic acid recovery column and water to a hydrolysis reactor for hydrolysis treatment. The bottom liquid composed mainly of water and methanol of the extractive distillation column is distilled by a methanol recovery column. The column top distillate of the methanol recovery column is recycled to the reaction-distillation column, and the water recovered from the column bottom is recycled to the extractive distillation column.

The hydrolyzed mixture leaving the hydrolysis reactor is introduced to a methyl acetate recovery column, and is distilled. The mixture composed mainly of unreacted methyl acetate and methanol coming off from the top of the methyl acetate recovery column is recycled to the extractive distillation column, and the mixture composed mainly of water and acetic acid obtained from the bottom of the methyl acetate recovery column is introduced to an acetic acid recovery column. The distillate mainly composed of water or aqueous acetic acid coming off from the column top of the acetic acid recovery column is recycled to the hydrolysis reactor.

The extractive distillation column, the methanol recovery column, the methyl acetate recovery column, and the acetic acid recovery column respectively are of any conventional type.

The ratio of the amount of water to be fed to the extractive distillation column relative to the amount of the mixture composed mainly of methyl acetate and methanol introduced form the reaction-distillation column is in the range of usually from 0.05 to 5 by weight, preferably from 0.1 to 1 by weight. With a less amount of water, the methanol concentration is higher in the distillate, and the methyl acetate concentration is higher in the column bottom liquid. With a larger amount of water, energy consumption increases uneconomically.

The water content of the methanol recovered from the top of the methanol recovery column is preferably as low as possible, and is usually not higher than 0.2% by weight, preferably not higher than 0.1% by weight, more preferably not higher than 0.05% by weight. The methanol concentration of the bottom liquid composed mainly of water of the methanol recovery column is not specially limited, but is desirably lower in order not to increase the amount of water introduced in the extractive distillation column and to decrease the recycling methanol.

The amount of water to be fed to the hydrolysis reactor depends on the amounts of the methyl acetate and methanol, and the hydrolysis ratio. The molar percentage of water to the methyl acetate is in the range of usually from 1 to 10, preferably from 1 to 5. The hydrolysis reaction catalyst include liquid acids such as sulfuric acid, phosphoric acid, and alkylsulfonic acid, and solid acids such as acidic cation exchange resin, silica, silica-alumina, and acid clay. Of these, acidic cation exchange resin is suitable in view of ease of handling after the reaction, and the apparatus construction materials.

The hydrolysis reactor may be any of stirring types, fixed bed types, and column types. For use of an acidic cation exchange resin as the catalyst, a fixed bed type reactor is suitable in which the catalyst is not damaged.

In another preferred embodiment, the acidic cation exchange resin molded into a shape causing less pressure drop or held in a container is incorporated in the distillation column to conduct the reaction and the distillation in one and the same column by reaction-distillation system, thereby the methyl acetate recovery column being omitted advantageously. The size of the apparatus depends on the required contact time. For a usual fixed bed type reactor, the contact time is in the range of usually from 0.03 to 10 hours, preferably from 0.1 to 5 hours. The reaction temperature is preferably in the range of from 50 to 120° C. in view of the reaction rate and heat resistance of the acidic cation exchange resin. The operation pressure of the reactor is not specially limited, but is usually in the range of from 1 to 5 atmosphere in terms of absolute pressure.

In the methyl acetate recovery column, the methyl acetate and methanol can be separated readily since the boiling point difference is sufficiently large between the distillate constituted mainly of methyl acetate and methanol and the column bottom liquid composed mainly of acetic acid and water. Therefore, the plate number and the reflux ratio are selected from the standpoint of economy. According to the present invention, the water distilled from the acetic acid recovery column is recycled to the hydrolysis reactor. This recycled water may contain acetic acid in a small amount in consideration of the process economy.

In the production of benzyl alcohol according to the present invention, the benzyl acetate is not limited in the production process thereof. For example, the benzyl acetate can be produced by oxyacetoxylation of toluene with acetic acid and oxygen continuously and efficiently by the process described before to produce high-purity benzyl acetate, and high-purity benzyl alcohol. In the process employing oxyacetoxylation, the acetic acid recovered from the bottom the acetic acid recovery column is recycled to the oxyacetoxylation reactor.

The embodiment of the transesterification process of the present invention is described below by reference to drawings. The embodiment includes various modifications, and the invention is not limited to the embodiment shown by the drawing.

Figure 7:
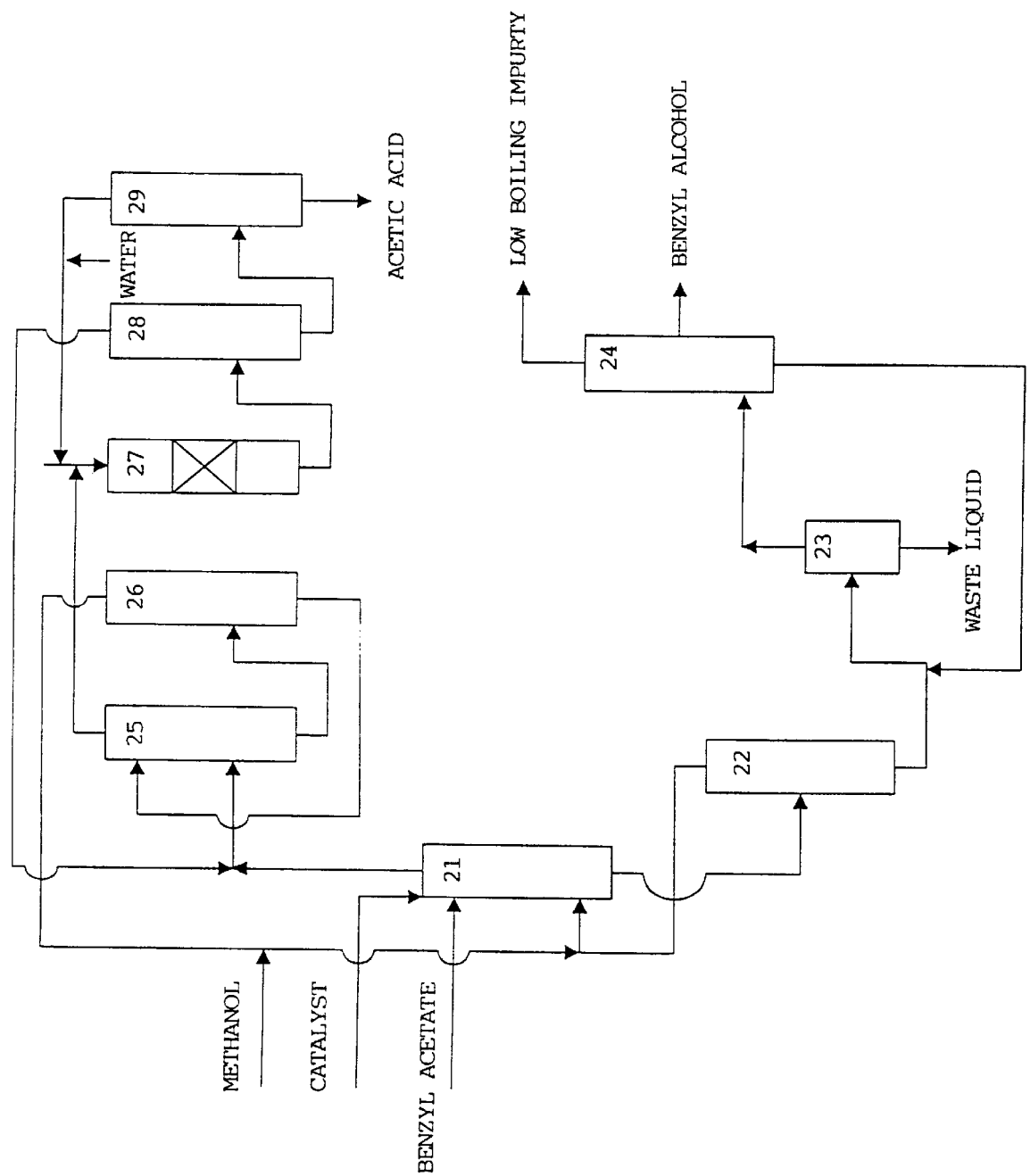
FIG. 7 is a flow sheet showing specifically an example of a process of transesterification in the production process of benzyl alcohol of the present invention.

FIG. 7 shows an example of the transesterification process of the present invention.

Benzyl acetate is fed to an upper portion of a reaction-distillation column 21, and methanol is fed to a lower portion of the same column 21, whereby the benzyl acetate and the methanol is brought into contact countercurrently in the presence of a basic catalyst to cause transesterification reaction.

Most portion of the methanol as the starting material is furnished by recycle of the methanol recovered from the column top of a methanol-separation column 22 of the later step and the methanol recovered from the column top of a methanol-recovery column 26 of the methyl acetate hydrolysis process, and small amount of methanol is replenished to make up an operation loss. The water concentration of the methanol is preferably controlled as described above.

The basic catalyst is fed to the same position as the benzyl acetate feed or a higher position than that. An enriching section comprising several plates is preferably provided above the benzyl acetate feed plate. By feeding the catalyst above the benzyl acetate feed plate, the reaction is caused also in the enriching section, which enables decrease of the enriching section plate number and of the reflux ratio corresponding to the reaction contribution in the enriching section.

The intended benzyl alcohol produced by the transesterification is discharged together with a part of excess methanol from the column of the reaction-distillation column 21, and is introduced to methanol separation column 22. The methanol separated by the distillation is discharged from the column top, and is recycled to the reaction-distillation column 21. When water is present in the methanol, the distillation conditions are preferably controlled to keep the water concentration in the methanol below the prescribed level.

The column bottom liquid of the methanol separation column 22 is introduced to a solid separator 23, where the liquid is concentrated to separate a solid. The solid separator 23 is exemplified by a thin film evaporator having a solid-scraper.

The vapor evaporated by the solid separator 23 is a mixture composed mainly of benzyl alcohol, and does not contain a solid component unless entrainment occurs. The vapor is introduced to an alcohol purification column 24. From the top of the purification column 24, low-boiling impurities are removed. High-purity benzyl alcohol is taken out from the middle portion of the alcohol purification column 24, and the bottom liquid of the column 24 is recycled to the solid separator 23. Naturally, the alcohol purification column 24 may be divided into two columns: a first distillation column for separating low-boiling separation and a second distillation column for taking out the product from the column top.

The mixture derived from the top of the reaction-distillation column 21 and composed mainly of methyl acetate and a part of excess methanol is introduced to the middle portion of an extractive distillation column 25 of the methyl acetate hydrolysis process. To the top of the extractive distillation column 25, the bottom liquid of a methanol recovery column 26 composed mainly of water is introduced to conduct extractive distillation of methanol with water. The mixture discharged from the bottom of the extractive distillation column 25 and composed mainly of water and methanol is introduced to the methanol recovery column 26. The mixture discharged from the bottom of the methanol recovery column 26 and composed mainly of water is recycled to the upper portion of the extractive distillation column 25. The distillate from the top of the methanol recovery column 26 and composed mainly of methanol is fed to the lower portion of the reaction-distillation column 21 together with the methanol recycled from methanol separation column 22 and the replenished methanol.

The column top liquid of the extractive distillation column 25 composed mainly of methyl acetate and water is fed together with the column top liquid of the acetic acid recovery column 29 mainly composed of water or water and acetic acid, and replenished water to the hydrolysis reactor 27. There, the methyl acetate is hydrolyzed. The effluent from the hydrolysis reactor 27 is introduced to a methyl acetate recovery column 28. By distillation in the methyl acetate recovery column 28, the mixture composed mainly of unhydrolyzed methyl acetate and methanol is taken out from the column top, and is recycled to the extractive distillation column 25. The bottom liquid of the methyl acetate recovery column 28 is introduced to an acetic acid recovery column 29.

As described above according to the present invention, high-purity benzyl alcohol can be produced stably and economically by transesterification of benzyl acetate with methanol.

The present invention is described in more detail by reference to examples without limiting the invention thereto. In the description below, "%" is based on weight, benzyl alcohol is denoted by "BzOH", and benzyl acetate is denoted by "BzOAc".

Example 1

This Example is explained by reference to FIG. 1.

An oxyacetoxylation reactor 1 was packed with 100 mL of a catalyst composed of a palladium-bismuth catalyst supported on spherical silica. To the reactor 1, were fed a liquid starting material composed of toluene, acetic acid, and recycling liquid recovered by distillation separation by a starting material recovery column 3 and a water removal column 7 (toluene: 59.7%, acetic acid 39.0%, and water: 1.2%) at a rate of 200.5 g/h; and air at a rate of 14.4 g/h and a recycling gas at a rate of 9.9 g/h (oxygen: 3.9%, and nitrogen: 92.6%) as the starting gas material, at a catalyst layer inlet temperature of 170° C. and a pressure of 14 kg/cm$^2$G to cause reaction.

As the results, 224.8 g/h of gas-liquid mixture effluent was obtained (composed of toluene: 47.4%, acetic acid: 31.4%, benzyl acetate: 8.3%, water: 2.2%, benzaldehyde: 0.3%, benzoic acid: 0.6%, benzyl benzoate: 0.2%, oxygen: 0.3%, and nitrogen: 9.0%). The temperature of the reactor outlet was 190° C.

The gas-liquid mixture effluent was introduced to a gas-liquid separator 2 to separate the gas and the liquid. The gas phase portion was partially condensed, and the condensate was combined with the liquid phase portion. The liquid phase portion was flash-evaporated at an atmospheric pressure. The generated vapor was condensed by cooling to 98° C. to obtain a condensate, and the condensate was combined with the liquid phase obtained by the flash-evaporation. Thus 117.2 g/h of a liquid effluent was obtained (the liquid composed of toluene: 46.2%, acetic acid: 36.1%, benzyl acetate: 15.2%, water: 0.3%, benzaldehyde: 0.6%, benzoic acid: 1.1%, and benzyl benzoate: 0.4%).

The liquid effluent was continuously introduced to a starting material recovery column 3 at a column top pressure of 130 Torr to obtain 95.6 g/h of a column top distillate (composed of toluene: 56.1%, acetic acid: 43.6%, and water: 0.4%), and 21.6 g/h of a column bottom liquid (composed of acetic acid: 1.4%, benzyl acetate: 86.0%, benzaldehyde: 3.2%, benzoic acid: 6.5%, and benzyl benzoate: 2.3%).

The bottom liquid of the starting material recovery column 3 was held temporarily in a vessel, and introduced to a low-boiler removal column 4 at a column top pressure of 40 Torr continuously at a rate of 107.9 g/h to obtain 4.3 g/h of a column top distillate (composed of toluene: 1.7%, acetic acid: 20.9%, and benzaldelyde: 77.3%), and 103.6 g/h of a column bottom liquid (benzyl acetate: 90.2%, benzoic acid: 6.8%, and benzyl benzoate: 2.4%).

Further, the column bottom liquid of the low-boiler removal column 4 was introduced continuously to a high-boiler removal column 5 at a column top pressure of 20 Torr to obtain 93.3 g/h of benzyl acetate having a purity of 99.8% from the column top.

Example 2

In a 200-mL round-bottomed flask, were placed 2.00 g (11.28 mmol) of palladium chloride (Wako Pure Chemical Industries, Ltd.) and 1.18 g (3.75 mmol) of bismuth chloride (Wako Pure Chemical Industries, Ltd.). Thereto, 43 mL of 6N hydrochloric acid was added, and the content in the flask was stirred at a room temperature until the palladium chloride and the bismuth chloride came to be completely dissolved. The atomic ratio of palladium and bismuth used was 3.0.

There, 40 g of silica (CARIACT-Q30, Fuji Silicia K.K.) having been dried at 180° C. for 2 hours (BET surface area: 100 m$^2$/g, pore volume: 1.05 cc/g, sphere shape of 3 mm diameter) was added, and the solution in the flask was impregnated into the silica by stirring the mixture until the liquid came to be completely absorbed.

After the impregnation, the water was removed under a reduced pressure by a rotary evaporator The obtained catalyst precursor was place in a heat-treatment tube, and treated for reduction by hydrogen gas flow of 50 mL/min at 400° C. for 5 hours.

The catalyst after the reduction treatment was washed with deionized water repeatedly until the chloride ion came to be not detected by the mercuric thiocyanate method. The washed catalyst was dried at 110° C. for 3 hours.

Figures 8, 9, 10:
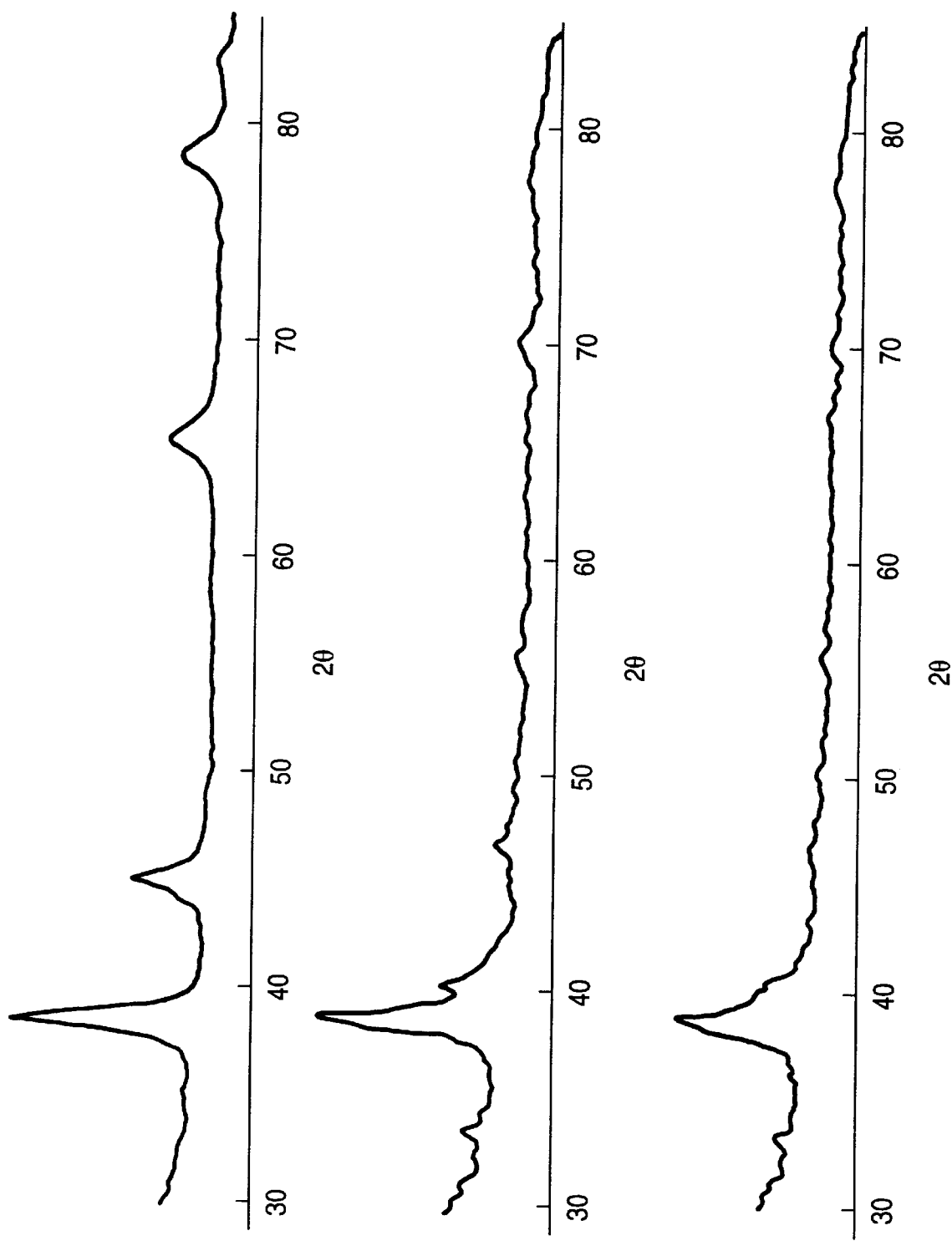
FIG. 8 is an XRD chart of the catalyst prepared in Example 2.
FIG. 9 is an XRD chart of the catalyst prepared in Comparative Example 1.
FIG. 10 is an XRD chart of the catalyst prepared in Comparative Example 2.

The obtained catalyst was analyzed by X-ray diffraction and was found that a palladium-bismuth alloy was formed in a palladium/bismuth atomic ratio of 3 as shown in FIG. 8.

This catalyst (10 cc) was mixed with 10 cc of glass beads of 1 mm diameter, and the mixture was packed in a SUS316 reaction tube of 13 mm inside diameter. Thereto, toluene (19.5 g/h), acetic acid (80.5 g/h), and oxygen (21 NmL/min), and nitrogen (79 NmL/min) were continuously fed to react at a reaction temperature of 150° C. at a pressure of 4 kg/cm²G.

The reaction product was separated into a liquid and a gas. The liquid component and the gas component were respectively analyzed by gas chromatography.

At the time after 5 hours from the start of the reaction, the time space yield of benzyl acetate (STY: produced amount of benzyl acetate per unit volume of catalyst per unit time) was 165 g/h/L and the selectivity was 98% for acetic acid.

From the general equation (7) below for catalyst deterioration, the time for dropping the STY of benzyl acetate by half was calculated to be about 1000 hours.

$$Ln(r/r0)=-kt \quad (7)$$

where r is an STY of benzyl acetate at a time t, r0 is an initial STY of benzyl acetate, and k is a catalyst deterioration constant.

A CO adsorption amount and a Pd elution rate at 50 hours after the start of the reaction is shown in Table 3.

Comparative Example 1

In a 200-mL round-bottomed flask, were placed 2.00 g (11.28 mmol) of palladium chloride (Wako Pure Chemical Industries, Ltd.) and 3.56 g (11.28 mmol) of bismuth chloride (Wako Pure Chemical Industries, Ltd.). Thereto, 43 mL of 12N hydrochloric acid was added, and the content in the flask was stirred at a room temperature until the palladium chloride and the bismuth chloride came to be completely dissolved.

There, 40 g of silica (CARIACT-Q30, Fuji Silicia K.K.) having been dried at 180° C. for 2 hours (BET surface area: 100 m²/g, pore volume: 1.05 cc/g, sphere shape of 3 mm diameter) was added, and the solution in the flask was impregnated into the silica by stirring the mixture until the liquid came to be completely absorbed.

After the impregnation, the water was removed under a reduced pressure by a rotary evaporator.

The obtained catalyst precursor was place in a heat-treatment tube, and treated for reduction by hydrogen gas flow of 50 mL/min at 400° C. for 5 hours.

The catalyst after the reduction treatment was washed with deionized water repeatedly until the chloride ion came to be not detected by the mercuric thiocyanate method. The washed catalyst was dried at 110° C. for 3 hours.

The obtained catalyst was analyzed by X-ray diffraction, and was found to be different from that obtained by Example 2 of the present invention as shown in FIG. 9.

The reaction and the analysis were conducted in the same manner as in Example 2 except that the above catalyst was used. The results are shown in Table 3.

Comparative Example 2

To 5.48 g (11.30 mmol) of bismuth nitrate pentahydrate (Wako Pure Chemical Industries, Ltd.), 43 mL of aqueous 7% nitric acid was added, and the bismuth nitrate pentahydrate was completely dissolved.

Thereto, 40 g of silica (CARIACT-Q30 Fuji Silicia K.K.) having been dried at 180° C. for 2 hours (BET surface area: 100 m²/g, pore volume: 1.05 cc/g, sphere shape of 3 mm diameter) was added, and the solution in the flask was impregnated into the silica by stirring the mixture until the liquid came to be completely absorbed.

After the impregnation, the water was removed under a reduced pressure by a rotary evaporator.

The obtained catalyst precursor was placed in a heat-treatment tube, and was calcined with a flow of air at a flow rate of 100 mL/min at 200° C. for 2 hours to obtain a silica-supported bismuth catalyst.

Separately, 1.90 g (10.71 mmol) of palladium chloride (Wako Pure Chemical Industries, Ltd.) was dissolved in 43 mL of 3N hydrochloric acid. Thereto the above silica-supported bismuth catalyst was added, and the solution was impregnated into the silica by stirring the mixture until the liquid came to be completely absorbed. After the impregnation, the water was removed under a reduced pressure by a rotary evaporator.

The obtained catalyst precursor was placed in a heat-treatment tube, and was dried with a flow of nitrogen at a flow rate of 100 mL/min at 150° C. for 2 hours. When the temperature of the catalyst layer dropped to a room temperature, the gas was changed to hydrogen at a flow rate of 50 mL/min to treat the catalyst precursor for reduction at 200° C. for 2 hours, and at 400° C. for 4 hours.

The catalyst after the reduction treatment was washed with deionized water repeatedly until the chloride ion came to be not detected by the mercuric thiocyanate method. The washed catalyst was dried at 110° C. for 3 hours.

The obtained catalyst was analyzed by X-ray diffraction, and was found to be different from that obtained by Example 2 of the present invention as shown in FIG. 10.

The reaction and the analysis were conducted in the same manner as in Example 2 except that the above catalyst was used. The results are shown in Table 3.

Comparative Example 3

To 2.74 g (5.65 mmol) of bismuth nitrite pentahydrate (Wako Pure Chemical Industries, Ltd.), 43 mL of aqueous 7% nitric acid solution was added, and the bismuth nitrate pentahydrate was completely dissolved.

Thereto, 40 g of silica (CARIACT-Q30, Fuji Silicia K.K.) having been dried at 180° C. for 2 hours (BET surface area: 100 m²/g, pore volume: 1.05 cc/g, sphere shape of 3 mm diameter) was added, and the solution was impregnated into the silica by stirring the mixture until the liquid came to be completely absorbed.

After the impregnation, the water was removed under a reduced pressure by a rotary evaporator. The solid matter was dried at 110° C. for 3 hours to obtain silica-supported bismuth nitrate.

Separately, 2.53 g (11.29 mmol) of palladium acetate (Wako Pure Chemical Industries, Ltd.) was dissolved in 43 mL of aqueous 3.5% ammonia solution. Thereto the above silica-supported bismuth nitrate was added, and the solution was impregnated into the silica by stirring the mixture until the liquid came to be completely absorbed. After the impregnation, the water was removed under a reduced pressure by a rotary evaporator.

The obtained catalyst precursor was placed in a heat-treatment tube, and was treated for reduction by hydrogen flow of 50 mL/min at 400° C. for 5 hours.

Figure 11:
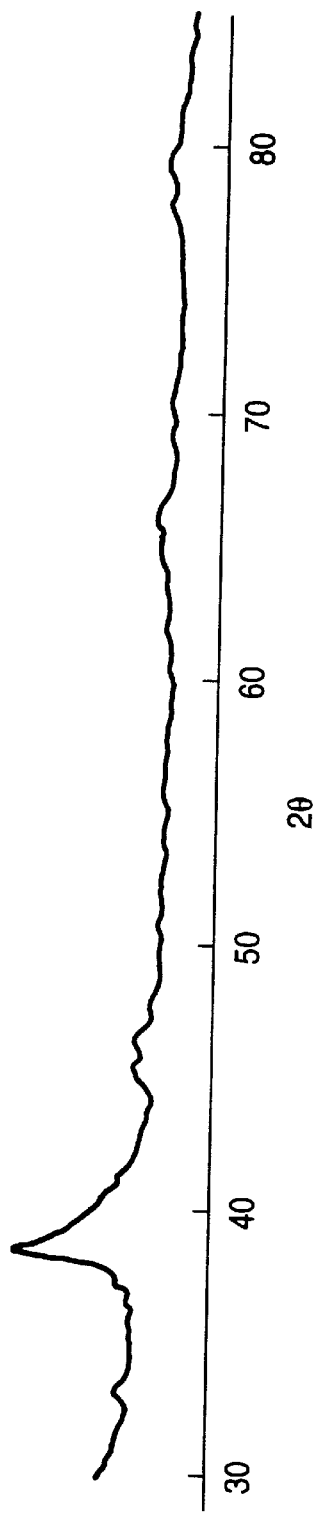
FIG. 11 is an XRD chart of the catalyst prepared in Comparative Example 3.

The obtained catalyst was analyzed by X-ray diffraction, and was found to be different from that obtained by Example 2 of the present invention as shown in FIG. 11.

The reaction and the analysis were conducted in the same manner as in Example 2 except that the above catalyst was used. The results are shown in Table 3.

Comparative Example 4

In a 200-mL round-bottomed flask, were placed 2.00 g (11.28 mmol) of palladium chloride (Wako Pure Chemical Industries, Ltd.) and 0.36 g (1.14 mmol) of bismuth chloride (Wako Pure Chemical Industries, Ltd.). Thereto, 43 mL of 6N hydrochloric acid was added, and the content in the flask was stirred at a room temperature to dissolve completely the palladium chloride and the bismuth chloride.

Thereto, 40 g of silica (CARIACT-Q30, Fuji Silicia K.K.) having been dried at 180° C. for 2 hours (BET surface area: 100 m$^2$/g, pore volume: 1.05 cc/g, sphere shape of 3 mm diameter) was added, and the solution in the flask was impregnated into the silica by stirring the mixture until the liquid came to be completely absorbed. After the impregnation, the water was removed under a reduced pressure by a rotary evaporator.

The obtained catalyst precursor was place in a heat-treatment tube, and treated for reduction by hydrogen gas flow of 50 mL/min at 400° C. for 5 hours.

The catalyst after the reduction treatment was washed with deionized water repeatedly until the chloride ion came to be not detected by the mercuric thicyanate method. The washed catalyst was dried at 110° C. for 3 hours.

Figure 12:
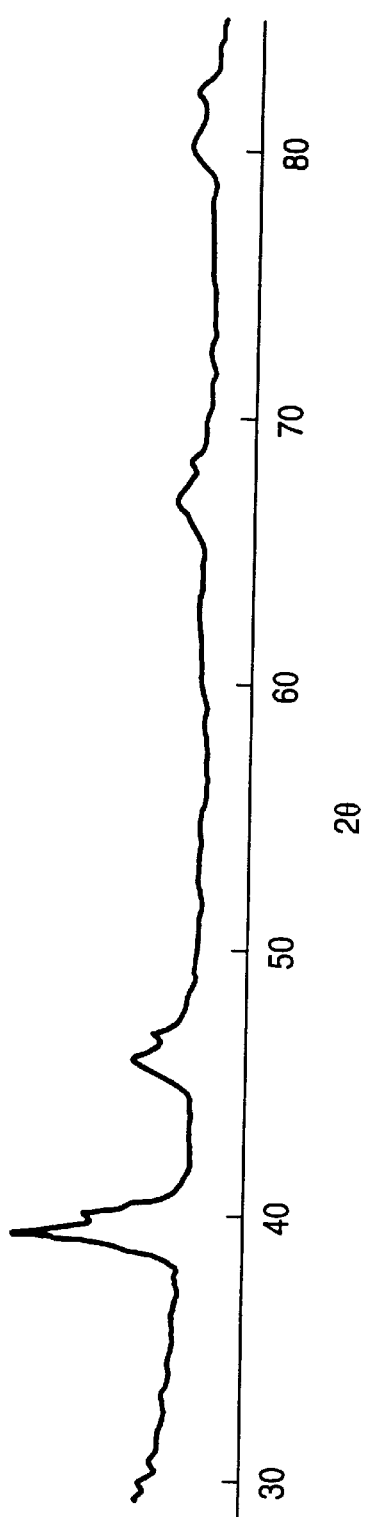
FIG. 12 is an XRD chart of the catalyst prepared in Comparative Example 4.

The obtained catalyst was analyzed by X-ray diffraction and was found that the X-ray diffraction pattern had peaks of Pd metal in addition to the peaks of the palladium-bismuth alloy of a palladium/bismuth atomic ratio of 3 as shown in FIG. 12, which is different from the catalyst obtained by Example 2 of the present invention.

The reaction and the analysis were conducted in the same manner as in Example 2 except that the above catalyst was used. The results are shown in Table 3.

Comparative Example 5

In a 200-mL round-bottomed flask, were placed 2.00 g (11.28 mmol) of palladium chloride (Wako Pure Chemical Industries, Ltd.). Thereto, 43 mL of 6N hydrochloric acid was added, and the content in the flask was stirred at a room temperature to dissolve completely the palladium chloride.

Thereto, 40 g of silica (CARIACT-Q30, Fuji Silicia K.K.) having been dried at 180° C. for 2 hours (BET surface area: 100 m$^2$/g, pore volume: 1.05 cc/g, sphere shape of 3 mm diameter) was added, and the solution in the flask was impregnated into the silica by stirring the mixture until the liquid came to be completely absorbed. Thereafter, the catalyst preparation was conducted in the same manner as in Example 2.

The reaction and the analysis were conducted in the same manner as in Example 2 except that the above catalyst was used. The results are shown in Table 3.

Comparative Example 6

In a 200-mL round-bottomed flask, were placed 1.18 g (3.74 mmol) of bismuth chloride (Wako Pure Chemical Industries, Ltd.). Thereto, 43 mL of 6N hydrochloric acid was added, and the content in the flask was stirred at a room temperature to dissolve completely the palladium chloride. Thereafter, the catalyst preparation was conducted in the same manner as in Example 2.

The reaction and the analysis were conducted in the same manner as in Example 2 except that the above catalyst was used. As the results, no benzyl acetate was found to be formed.

Example 3

Ten milliliters of the catalyst prepared in Example 2 was packed in a SUS316 reaction tube of 13 mm inside diameter. Thereto, toluene (2.2 g/min), acetic acid (1.4 g/min), oxygen (23.3 NmL/min), and nitrogen (396 NmL/min) were continuously fed to react at a reaction temperature of 170° C. at a pressure of 14 kg/cm$^2$G. During the reaction, the oxygen partial pressure was 0.6 kg/cm$^2$ in the gas phase in the reactor.

The reaction product was separated into a liquid and a gas. The liquid component and the gas component were respectively analyzed by gas chromatography.

At a time after 3 hours from the start of the reaction, the time space yield STY of benzyl acetate was 313 g/h/L and the selectivity was 98% for acetic acid.

No elution of palladium into the reaction liquid was found by measurement by flameless atomic absorption spectrometry.

Comparative Example 7

The reaction and the product analysis were conducted in the same manner as in Example 3 except that the same lot of the catalyst prepared in Comparative Example 5 was used. The results are shown collectively in Table 4.

Example 4

The reaction and the product analysis were conducted in the same manner as in Example 3 except that the same lot of the catalyst prepared in Example 2 was used, and the continuous material feed rates were changed to toluene: 2.2 g/min, acetic acid: 1.4 g/min, oxygen: 38.5 NmL/min, and nitrogen: 381 NmL/min (the oxygen partial pressure: 1.0 kg/cm$^2$ in the gas phase in the reaction system). The results are shown collectively in Table 4.

Example 5

The reaction and the product analysis were conducted in the same manner as in Example 3 except that the same lot of the catalyst prepared in Example 2 was used, and the continuous material feed rates were changed to toluene: 2.2 g/min, acetic acid: 1.4 g/min, oxygen: 58.3 NmL/min, and nitrogen: 361 NmL/min (the oxygen partial pressure: 1.5 kg/cm$^2$ in the gas phase in the reaction system). The results are shown collectively in Table 4.

Example 6

The reaction and the product analysis were conducted in the same manner as in Example 3 except that the same lot of the catalyst prepared in Example 2 was used, and the continuous material feed rates were changed to toluene: 2.8 g/min, acetic acid: 1.8 g/min, oxygen: 58.3 NmL/min, and nitrogen: 990 NmL/min (the oxygen partial pressure: 0.6 kg/cm$^2$ in the gas phase in the reaction system). The results are shown collectively in Table 4.

Example 7

The reaction and the product analysis were conducted in the same manner as in Example 3 except that the same lot of the catalyst prepared in Example 2 was used, and the continuous material feed rates were changed to toluene: 2.2 g/min, acetic acid: 1.4 g/min, oxygen: 87.5 NmL/min, and nitrogen: 332 NmL/min (the oxygen partial pressure: 2.25 kg/cm$^2$ in the gas phase in the reaction system). The results are shown collectively in Table 4.

Example 8

The reaction and the product analysis were conducted in the same manner as in Example 3 except that the same lot of the catalyst prepared in Example 2 was used, and the continuous material feed rates were changed to toluene: 2.2 g/min, acetic acid: 1.4 g/min, oxygen: 117 NmL/min, and nitrogen: 303 NmL/min (the oxygen partial pressure: 3.0 kg/cm$^2$ in the gas phase in the reaction system). The results are shown collectively in Table 4.

Example 9

Ten milliliters of the catalyst prepared in Example 2 and 10 mL of glass beads of 1 mm diameter were mixed, and was packed in a SUS316 reaction tube of 13 mm inside diameter. Thereto, toluene (0.14 g/min), acetic acid (0.1 g/min), oxygen (2.7 NmL/min: 0.7 mol/h per liter of catalyst), and nitrogen (209 NmL/min) were continuously fed to allow the reaction to proceed at a temperature of 170° C. at a pressure of 44 kg/cm$^2$G.

The reaction product was separated into a liquid and a gas. The liquid component and the gas component were respectively analyzed by gas chromatography.

At a time after 20 hours from the start of the reaction, the time space yield STY of benzyl acetate was 83 g/h/L and the selectivity was 95% for acetic acid.

According to the general equation (7) of catalyst deterioration, the time for dropping the STY of benzyl acetate by half was calculated to be more than 10000 hours.

Example 10

The reaction and the product analysis were conducted in the same manner as in Example 9 except that the same lot of the catalyst prepared in Example 2 was used, and the continuous material feed rates were changed to toluene: 0.14 g/min, acetic acid: 0.1 g/min, oxygen: 7.8 NmL/min (2.1 mol/h per liter of catalyst), and nitrogen: 204 NmL/min. The results are shown collectively in Table 5.

Example 11

The reaction and the product analysis were conducted in the same manner as in Example 9 except that the same lot of the catalyst prepared in Example 2 was used, and the continuous material feed rates were changed to toluene: 0.14 g/min, acetic acid: 0.1 g/min, oxygen: 15.6 NmL/min (4.2 mol/h per liter of catalyst), and nitrogen: 196 NmL/min. The results are shown collectively in Table 5.

Example 12

The reaction and the product analysis were conducted in the same manner as in Example 9 except that the same lot of the catalyst prepared in Example 2 was used, the reaction pressure was changed to 14 kg/cm$^2$G, and the continuous material feed rates were changed to toluene: 0.3 g/min, acetic acid: 0.2 g/min, oxygen: 5.8 NmL/min (1.6 mol/h per liter of catalyst), and nitrogen: 51 NmL/min. The results are shown collectively in Table 5.

Example 13

The reaction and the product analysis were conducted in the same manner as in Example 8 except that the same lot of the catalyst prepared in Example 2 was used, and the continuous material feed rates were changed to toluene: 0.14 g/min, acetic acid: 0.1 g/min, oxygen: 20.7 NmL/min (5.5 mol/h per liter of catalyst), and nitrogen: 191 NmL/min. The results are shown collectively in Table 5.

Example 14

The reaction and the product analysis were conducted in the same manner as in Example 9 except that the same lot of the catalyst prepared in Example 2 was used, and the continuous material feed rates were changed to toluene: 0.14 g/min, acetic acid: 0.1 g/min, oxygen: 1.5 NmL/min (0.4 mol/h per liter of catalyst), and nitrogen: 210 NmL/min. The results are shown collectively in Table 5.

Example 15

The reaction and the product analysis were conducted in the same manner as in Example 3 except that the feed rates of toluene and acetic acid are changed to toluene: 3.1 g/min, and acetic acid: 0.4 g/min (ratio of acetic acid/toluene=0.25 (mole ratio)). The results are shown in Table 6.

Example 16

The reaction and the product analysis were conducted in the same manner as in Example 3 except that the feed rates of toluene and acetic acid are changed to toluene: 1.0 g/min, and acetic acid: 2.7 g/min (ratio of acetic acid/toluene=4 (mole ratio)). The results are shown collectively in Table 6.

Example 17

The reaction and the product analysis were conducted in the same manner as in Example 3 except that the feed rates of toluene and acetic acid are changed to toluene: 3.4 g/min, and acetic acid: 0.2 g/min ratio of acetic acid/toluene=0.11 (mole ratio)). The results are shown collectively in Table 6.

Example 18

The reaction and the product analysis were conducted in the same manner as in Example 3 except that the feed rates of toluene and acetic acid are changed to toluene: 0.1 g/min, and acetic acid: 3.6 g/min (ratio of acetic acid/toluene=49 (mole ratio)). The results are shown collectively in Table 6.

Example 19

Into a SUS316 reaction tube of inside diameter of 13 mm, was packed 10 cc of the catalyst prepared in the same manner as in Example 2. 0.01 Gram of bismuth oxide as a soluble bismuth compound was dissolved in 19 kg of an equimolar mixture of toluene and acetic acid (bismuth weight ratio: 5×10$^{-7}$ in terms of bismuth metal in the liquid mixture).

To the reaction tube packed with the catalyst, were fed the liquid mixture of toluene and acetic acid containing bismuth oxide dissolved therein (3.65 g/min), oxygen (23.3 NmL/min), and nitrogen (396 NmL/min) at a reaction temperature of 170° C. at a reaction pressure of 14 kg/cm$^2$G to conduct the reaction.

The space time yield (STY) of benzyl acetate was 286 g/h/L at the reaction time of 3 hours, and this STY was maintained for 300 hours without drop. During the above reaction, palladium was not detected in the reaction liquid mixture. The results are shown in Table 7.

Example 20

The reaction and the analysis were conducted in the same manner as in Example 19 except that the amount of the bismuth used was 0.001 g (bismuth weight ratio: 5×10$^{-8}$ in terms of bismuth metal in the liquid mixture). The results are shown collectively in Table 7.

Example 21

The reaction and the analysis were conducted in the same manner as in Example 19 except that 0.02 g of bismuth nitrate pentahydrate was used as the soluble bismuth compound (bithmuth weight ratio: $5\times10^{-7}$ in terms of bismuth metal in the liquid mixture). The results are shown collectively in Table 7.

Example 22

Into a SUS316 reaction tube of inside diameter of 28 mm, was packed 10 cc of the catalyst prepared in the same manner as in Example 2.

0.13 Gram of bismuth oxyacetate as a soluble bismuth compound was dissolved in 19 kg of an equimolar mixture of toluene and acetic acid (bismuth weight ratio: $5\times10^{-6}$ in terms of bismuth metal in the liquid mixture).

To the reaction tube packed with the catalyst, were fed the liquid mixture of toluene and acetic acid containing bismuth oxyacetate dissolved therein (3.65 g/min), oxygen (47 NmL/min), and nitrogen (372 NmL/min) at a reaction temperature of 170° C. at a reaction pressure of 14 kg/cm$^2$G to conduct the reaction.

The reaction mixture was separated into a gas phase and a liquid phase, and the gas phase and the liquid phase were respectively analyzed by gas chromatography. The results are shown in Table 7 collectively.

Example 23

Benzyl alcohol was produced by the hydrolysis reaction process shown in FIG. 2.

1,080 Milliliters of Amberlist 31 Wet (Japan Organo Co., Ltd.), a sulfonated acid type cation exchange resin (styrene-divinylbenzene copolymer of divinylbenzene unit content of 4%) was packed to a hydrolysis reactor 9. To this reactor 9, a starting material mixture (composed of BzOAc: 72.2%, water: 18.3%, BzOH: 6.6%, and acetic acid: 2.8%) at an LHSV of 0.27 h$^{-1}$ to allow the reaction to proceed at 90° C.

Thereby, a liquid reaction mixture (composed of BzOH: 32.6%, BzOAc: 36.1%, acetic acid: 17.2%, and water: 14.0%) was obtained at a rate of 241.3 g/h.

This liquid reaction mixture was introduced to an acetic acid-water recovery column 10, and distillation was conducted at a pressure of 50 Torr to obtain an aqueous acetic acid solution from the column top at a rate of 75.4 g/h.

The bottom liquid of the acetic acid-water recovery column 10 (composed of BzOH: 47.4%, and BzOAc: 52.5%) was continuously introduced to an alcohol concentration column 11, and the distillation was conducted at an ordinary pressure to obtain 21.7 g/h of BzOH from the column top with a purity of 99.0%, and 144.3 g/h of a column bottom liquid (composed of BzOAc: 60.3%, and BzOH: 39.6%).

Example 24

Benzyl alcohol was produced by the hydrolysis reaction process shown in FIG. 3.

The reaction was conducted in the same manner as in Example 23 by use of the hydrolysis reactor 9. The obtained liquid reaction mixture (composed of BzOH: 32.6%, BzOAc: 36.1%, acetic acid: 17.2%, water: 14.0%) was introduced to a liquid-liquid separator 14 to allow the mixture to separate at 30° C. into an organic phase (composed of BzOH: 34.3%, BzOAc: 38.4%, acetic acid: 16.7%, and water: 10.4%) and an aqueous phase (composed of BzOH: 6.3%, BzOAc: 1.1%, acetic acid: 25.0%, and water: 67.5%). The aqueous phase was recycled to the hydrolysis reactor 9.

The organic phase separated by the liquid-liquid separator 14 was introduced to an acetic acid-water recovery column 10, and distillation was conducted at a pressure of 50 Torr to obtain an aqueous acetic acid solution from the column top at a rate of 61.5 g/h.

The bottom liquid of the acetic acid-water recovery column 10 (composed of BzOH: 47.2%, and BzOAc: 52.8%) was continuously introduced to an alcohol concentration column 11, and the distillation was conducted at an ordinary pressure to obtain 21.7 g/h of BzOH of 99.0% purity from the column top, and 143.1 g/h of a column bottom liquid (composed of BzOAc: 60.6%, and BzOH: 39.3%).

Example 25

The hydrolysis reactor 9 and the acetic acid-water recovery column 10 were conducted in the same manner as in Example 23, and the resulting benzyl alcohol was purified by azeotropic distillation with water as shown in FIG. 4.

The bottom liquid discharged from the acetic acid-water recovery column 10 (composed of BzOH: 47.7%, and BzOAc: 52.5%) was continuously introduced to the alcohol concentration column 11 and distilled at an ordinary pressure. The bottom liquid composed mainly of BzOAc and containing a small amount of BzOH was discharged at a rate of 97.6 g/h.

The column top distillate of the alcohol concentration column 11 (composed of BzOH: 92.9%, BzOAc: 7.1%) was introduced continuously to the first alcohol purification column 15 and was distilled with introduction of water (43.2 g/h) at atmospheric pressure. Thereby, an organic phase composed mainly of BzOAc and containing a small amount of BzOH and water, and an aqueous phase composed mainly of water were distilled out at a rate respectively of 13.0 g/h and 42.1 g/h from the liquid-liquid separator 17 equipped at the column top portion.

The bottom liquid (composed of BzOH: 96.1%, and water: 3.7%) of the first alcohol purification column 15 was introduced continuously to the second alcohol purification column 16, and was distilled at a pressure of 100 Torr to obtain BzOH of purity of 99.8% from the column bottom at a rate of 54.1 g/h and a column top distillate composed mainly of water from the column top at a rate of 2.4 g/h.

Example 26

The hydrolysis reactor 9, the acetic acid-water recovery column 10, and the alcohol concentration column 11 were conducted driven in the same manner as in Example 23, and the resulting benzyl alcohol was purified by extractive distillation with glycerin as shown in FIG. 5

The column top liquid of the alcohol concentration column 11 (composed of BzOH: 92.9%, and BzOAc: 7.1%) was introduced continuously to the extractive distillation column 18, and glycerin is introduced to the upper portion of the extractive distillation column 18 at a rate of 176.6 g/h. Extractive distillation was conducted at a pressure of 50 Torr to obtain a distillate (composed of BzOAc: 68.7%, BzOH: 29.7%, and glycerin 1.4%) from the column top at a rate of 6.9 g/h. Water was added to the distillate, and the mixture was separated by the liquid-liquid separator 20 to obtain an organic phase composed mainly of BzOAc and containing a small amount of BzOH and water, and an aqueous phase composed mainly of water at a rate respectively of 6.9 g/h, and 3.6 g/h.

The bottom liquid of the extractive distillation column 18 (composed of BzOH: 25.8%, and glycerin: 74.1%) was introduced to the product column 19, and distillation was conducted at a pressure of 50 Torr to obtain BzOH of 99.9% purity from the column top at a rate of 61.5 g/h, and a column bottom liquid mainly composed of glycerin at a rate of 176.5 g/h.

Example 27

Benzyl alcohol was produced by the hydrolysis reaction process as shown in FIG. 4.

Into the hydrolysis reactor 9, was packed 1,080 mL of Amberlist 31 Wet (Japan Organo Co., Ltd.) which is a sulfonated acid type cation exchange resin based on a styrene-vinylbenzene copolymer of divinylbenzene unit content of 4%. To this reactor, were fed fresh BzOAc (88.2 g/h), an aqueous 19.5% acetic acid solution obtained as a side stream from the top portion of the acetic acid-water separation column 12 (56.7 g/h), and a bottom liquid of the alcohol concentration column 11 (142.8 g/h, composed of BzOAc: 94.0% and BzOH: 6.0%), and the reaction was allowed to proceed at 80° C. Thereby, a reaction liquid (composed of BzOH: 24.3%, BzOAc: 46.8%, acetic acid: 16.7%, and water: 12.2%) was obtained at a rate of 287.7 g/h.

The reaction liquid was introduced to the acetic acid-water recovery column 10, and distillation was conducted at a pressure of 50 Torr to obtain an aqueous acetic acid solution from the column top at a rate of 83.8 g/h.

The bottom liquid of the acetic acid-water recovery column 10 (composed of BzOH: 33.8%, and BzOAc: 66.2%) was introduced continuously to the alcohol concentration column 11, and distillation was conducted at a pressure of 95 Torr to obtain a bottom liquid composed mainly of BzOAc and a small amount of BzOH at a rate of 142.8 g/h.

The column top distillate of the alcohol concentration column 11 (composed of BzOH: 75.8%, and BzOAc: 24.2%) was introduced continuously to the first alcohol purification column 15, and was distilled with introduction of water (0.8 g/h) at atmospheric pressure. Thereby, an organic phase composed mainly of BzOAc and containing a small amount of BzOH and water, and an aqueous phase composed mainly of water were discharged at a rate respectively of 32.0 g/h and 81.3 g/h from the liquid-liquid separator 17 equipped at the column top portion. The organic phase was recycled to the acetic acid-water recovery column 10, and the aqueous phase was recycled to the first alcohol purification column 15.

The bottom liquid of the first alcohol purification column 15 (composed of BzOH: 92.7%, and water: 7.3%) was introduced continuously to the second alcohol purification column 16, and distillation was conducted at a pressure of 100 Torr to obtain BzOH of 99.9% purity from the column bottom at a rate of 63.4 g/h and a distillate composed mainly of water from the column top at a rate of 5.1 g/h. This distillate was recycled to the first alcohol concentration column 15.

Example 28

Into a flow reactor equipped with a temperature controller, was packed a sulfonic acid type cation exchange resin (based on a styrene-divinylbenzene copolymer) having a divinylbenzene content (DVB content) shown in Table 8. To this reactor, benzyl acetate and water as the starting materials (mole ratio of water/benzyl acetate=63/37) was fed at 80° C. at LHSV of 0.45 h$^{-1}$ to cause reaction. The conversion of the benzyl acetate (BC) and the selectivity of the benzyl alcohol (BS) were measured by gas chromatography. The results are shown in Table 8.

The reaction was continued for 1,000 hours under the above conditions, and the activity deterioration coefficient (rate of drop of benzyl acetate conversion per hour) was measured, but no activity deterioration was observed.

Examples 29–30 and Comparative Examples 8–11

Into a flow reactor equipped with a temperature controller, was packed a sulfonic acid type cation exchange resin (based on a styrene-divinylbenzene copolymer) having a divinylbenzene content (DVB content) shown in Table 8 such that the amount of the sulfonic acid group is the same as in Example 28. The reaction was conducted in the same manner as in Example 28. The conversion ratio of the benzyl acetate (BC) and the selectivity of the benzyl alcohol (BS) were measured by gas chromatography in the same manner as in Example 28. The results are shown collectively in Table 8.

In Comparative Example 11, the activity deterioration coefficient was measured by continuing the reaction for 1,000 hours under the same reaction as in Example 28, and was found to be 0.002% per hour.

Example 31

Into a flow reactor equipped with a temperature controller, was packed 22.07 g of Amberlist 31 Wet (Japan Organo Co., Ltd.) which is a sulfonic acid type cation exchange resin based on a styrene-vinylbenzene copolymer of divinylbenzene unit content of 4%. To this reactor, the starting materials shown in Table 9 were fed at 80° C. at LHSV of 0.45 h$^{-1}$ to cause reaction. The reaction product was analyzed quantitatively by gas chromatography, from which were calculated the conversion (BC) of the benzyl acetate (BzOAc), the selectivity (BS) of the benzyl alcohol, and the reaction productivity (STY); space time yield represented by grams of benzyl alcohol per liter of the wet resin per hour. Table 9 shows the results. Table 9 also shows the mole ratio of dibenzyl ether (BzOBz), a reaction by-product, to the benzyl alcohol, the weight ratio (W/B) of water to benzyl alcohol in the produced liquid which is an index of the load in the benzyl alcohol separation-recovery process, and the estimated equilibrium conversion.

Examples 32–34 and Comparative Examples 12–14

The hydrolysis reaction was conducted in the same manner as in Example 31 except that the composition of the starting materials fed to the reactor was charged as shown in Table 9. The results are shown in Table 9 collectively.

Example 35

The hydrolysis reaction was conducted in the same manner as in Example 31 except that the cation exchange resin was replaced by XT-2071 (Japan Organo Co., Ltd.) which is a sulfonated acid type cation exchange resin based on a styrene-vinylbenzene copolymer of divinylbenzene unit content of 7% in an equivalent amount of the sulfonated acid group; the composition of the starting materials was as shown in Table 9; and LHSV was 0.39 h$^{-1}$. The results are shown in Table 9.

Example 36

This example is described by reference to FIG. 7.

Benzyl acetate of 99.7% purity (containing benzaldehyde: 0.03%, benzyl alcohol: 0.24 %, acetic acid: 0.01%, benzoic acid: 0.01%, and water: 0.01%) was fed continuously at a rate of 427 g/h to the top of a reaction-distillation column 21 (having 30 plates: 25 plates for the reactor portion). Methanol recovered from the top of a methanol separation column 22 and the top of a methanol recovery column 26, and replenished methanol were fed to the fifth plate of the reaction distillation column 21 at a total feed rate of 242 g/h (fed methanol containing methyl acetate: 0.16%, and water: 0.01%). Further, as the catalyst, a methanol solution containing 2% sodium methylate was fed to the top of the column at a feed rate of 13.8 g/h. The operation temperature of the bottom of the column was 96.0° C.

From the bottom of the reaction-distillation column, the reaction mixture was obtained at a rate of 349 g/h (composed of benzyl alcohol: 86.8%, and methanol: 13.1%). The gas chromatogram of this reaction mixture showed only a trace of the peak of starting benzyl acetate.

The reaction mixture was introduced to a methanol separation column 22, and distillation was conducted to obtain methanol as the distillate at a rate of 44 g/h. This methanol was recycled to the reaction-distillation column 21. The bottom liquid of the methanol separation column 22 was stored in a receiver. 5.0 Kilograms of the bottom liquid was charged to a solid separator 23 of a rotary thin film evaporator type, and was evaporated and concentrated by changing the pressure stepwise from 350 to 100 Torr to obtain 4.9 kg of benzyl alcohol of 99.8% purity.

From the top of the reaction distillation column 21, a distillate was obtained at a rate of 334 g/h (the distillate composed of methyl acetate: 62.5%, methanol: 35.7%, benzyl acetate: 0.9%, and benzyl alcohol: 0.9%). This distillate was combined with the distillate of the methyl acetate recovery column 28, and the mixture was introduced to the middle portion of an extractive distillation column 25. Extractive distillation was conducted with feeding of water from the top of the column at a feed rate of 177 g/h. The bottom liquid of the extractive distillation was introduced to the methanol recovery column 26, and distilled. The distillate (composed of methanol: 99.8%, and methyl acetate: 0.2%) discharged from the column top at a rate of 205 g/h was recycled to the reaction-distillation column 21.

The distillate (635 g/h) from the top of the extractive distillation column 25 (composed of methyl acetate: 95.5%, methanol: 2.0%, and water: 2.5%) was mixed with the distillate (454 g/h) from the acetic acid recovery column 29 (composed of water: 69.6%, and acetic acid: 30.0%) and water (109 g/h), and the mixture was introduced to a hydrolysis reactor 27. The hydrolysis reactor 27 was a tube of an inside diameter of 4 cm, and height of 80 cm having a fixed glass bed, and was filled with 1000 mL of H-type Amberlite IR-120B (Japan Organo Co., Ltd.), a commercial acidic cation exchange resin. The hydrolysis was conducted at 40° C.

The reaction mixture discharged from the hydrolysis reactor 27 was introduced to a methyl acetate recovery column 28 and was distilled. The distillate (557 g/h) from the column top (composed of methyl acetate: 71.5%, methanol: 18.5%, and water: 10%) was recycled to the extractive distillation column 25, and the bottom liquid was introduced to an acetic acid recovery column 29, and was distilled. The distillate from the acetic acid recovery column 29 was recycled to the hydrolysis reactor, and from the bottom, aqueous 90% acetic acid solution was recovered at a rate of 18.8 g/h.

TABLE 1

| 2θ (°) | Peak intensity ratio* |
|---|---|
| 38.5 ± 0.3 | 100 |
| 44.8 ± 0.3 | 35 ± 20 |
| 65.4 ± 0.3 | 20 ± 10 |
| 78.6 ± 0.3 | 20 ± 10 |

CuKα, 40 kV, 200 mA
*Relative intensity to the main peak taken as 100

TABLE 2

| | BzOAc (wt %) | Water (wt %) | Acetic acid (wt %) |
|---|---|---|---|
| A | 63.0 | 7.0 | 30.0 |
| B | 90.0 | 10.0 | 0.0 |
| C | 40.0 | 60.0 | 0.0 |
| D | 28.0 | 42.0 | 30.0 |
| E | 72.0 | 8.0 | 20.0 |
| F | 60.0 | 40.0 | 0.0 |

TABLE 3

| | STY (g/h/L) | Selectivity (%) | Half-life (h) | Pd elution rate (µg/h) | CO Adsorption (cc/g) |
|---|---|---|---|---|---|
| Example | | | | | |
| 2 | 165 | 98 | 1000 | 3 | 0.00 |
| Comparative Example | | | | | |
| 1 | 226 | 98 | 165 | 14 | 0.00 |
| 2 | 230 | 97 | 165 | 14 | 0.00 |
| 3 | 150 | 98 | 200 | 10 | 0.00 |
| 4 | 78 | 98 | 50 | 10 | 0.03 |
| 5 | 121 | 94 | 24 | 100 | 1.60 |
| 6 | 0 | 0 | — | — | 0.00 |

TABLE 4

| | Catalyst (cc) | Reaction temperature (° C.) | Reaction pressure (kg/cm²G) | Feed rate | | Oxygen partial pressure (kg/cm²) | STY (g/h/L) | Selectivity (%) | Pd elution rate (µg/h) |
|---|---|---|---|---|---|---|---|---|---|
| Example 3 | 10 | 170 | 14 | Toluene<br>Acetic acid<br>Oxygen<br>Nitrogen | 2.2 g/m<br>1.4 g/m<br>23.2 MmL/m<br>396 NmL/m | 0.6 | 313 | 98 | Not detected |
| Comparative | 10 | 170 | 14 | Toluene<br>Acetic acid | 2.2 g/m<br>1.4 g/m | 0.6 | 160 | 79 | 184 |

TABLE 4-continued

| | Catalyst (cc) | Reaction temperature (° C.) | Reaction pressure (kg/cm²G) | Feed rate | | Oxygen partial pressure (kg/cm²) | STY (g/h/L) | Selectivity (%) | Pd elution rate (μg/h) |
|---|---|---|---|---|---|---|---|---|---|
| example 7 | | | | Oxygen<br>Nitrogen | 23.2 MmL/m<br>396 NmL/m | | | | |
| Example 4 | 10 | 170 | 14 | Toluene<br>Acetic acid<br>Oxygen<br>Nitrogen | 2.2 g/m<br>1.4 g/m<br>38.5 MmL/m<br>381 NmL/m | 1.0 | 441 | 95 | 3 |
| Example 5 | 10 | 170 | 14 | Toluene<br>Acetic acid<br>Oxygen<br>Nitrogen | 2.2 g/m<br>1.4 g/m<br>58.3 MmL/m<br>361 NmL/m | 1.5 | 566 | 94 | 33 |
| Example 6 | 10 | 170 | 14 | Toluene<br>Acetic acid<br>Oxygen<br>Nitrogen | 2.8 g/m<br>1.8 g/m<br>58.3 MmL/m<br>990 NmL/m | 0.6 | 366 | 95 | Not detected |
| Example 7 | 10 | 170 | 14 | Toluene<br>Acetic acid<br>Oxygen<br>Nitrogen | 2.2 g/m<br>1.4 g/m<br>87.5 MmL/m<br>332 NmL/m | 2.25 | 752 | 94 | 230 |
| Example 7 | 10 | 170 | 14 | Toluene<br>Acetic acid<br>Oxygen<br>Nitrogen | 2.2 g/m<br>1.4 g/m<br>117 MmL/m<br>303 NmL/m | 3.0 | 837 | 95 | 570 |

TABLE 5

| | Catalyst (cc) | Reaction temperature (° C.) | Reaction pressure (kg/cm²G) | Feed rate | | Oxygen feed (mol/L/h) | STY (g/h/L) | Selectivity (%) | Activity half life (h) |
|---|---|---|---|---|---|---|---|---|---|
| Example 9 | 10 | 170 | 44 | Toluene<br>Acetic acid<br>Oxygen<br>Nitrogen | 0.14 g/m<br>0.1 g/m<br>2.7 MmL/m<br>209 NmL/m | 0.7 | 83 | 95 | >10000 |
| Example 10 | 10 | 170 | 44 | Toluene<br>Acetic acid<br>Oxygen<br>Nitrogen | 0.14 g/m<br>0.1 g/m<br>7.8 MmL/m<br>204 NmL/m | 2.1 | 185 | 95 | 5000 |
| Example 11 | 10 | 170 | 44 | Toluene<br>Acetic acid<br>Oxygen<br>Nitrogen | 0.14 g/m<br>0.1 g/m<br>15.6 MmL/m<br>196 NmL/m | 4.2 | 275 | 95 | 2000 |
| Example 12 | 10 | 170 | 14 | Toluene<br>Acetic acid<br>Oxygen<br>Nitrogen | 0.3 g/m<br>0.2 g/m<br>5.8 MmL/m<br>51 NmL/m | 1.6 | 201 | 98 | >10000 |
| Example 13 | 10 | 170 | 44 | Toluene<br>Acetic acid<br>Oxygen<br>Nitrogen | 0.14 g/m<br>0.1 g/m<br>20.7 MmL/m<br>191 NmL/m | 5.5 | 283 | 95 | 1000 |
| Example 14 | 10 | 170 | 44 | Toluene<br>Acetic acid<br>Oxygen<br>Nitrogen | 0.14 g/m<br>0.1 g/m<br>1.5 NmL/m<br>210 NmL/m | 0.4 | 40 | 95 | >10000 |

TABLE 6

| | Acetic acid/toluene (Mole ratio) | STY (g/h/L) | Pd elution |
|---|---|---|---|
| Example 3 | 1 | 313 | Not detected |
| Example 15 | 0.25 | 212 | Not detected |
| Example 16 | 4 | 304 | Not detected |
| Example 17 | 0.1 | 125 | Not detected |
| Example 18 | 49 | 130 | Not detected |

TABLE 7

|  | Soluble bismuth compound | Amount of bismuth in liquid mixture* | STY (g/h/L) | Deterioration in STY** | Pd elution |
|---|---|---|---|---|---|
| Example 19 | Bismuth oxide | $5 \times 10^{-7}$ | 286 | None | Not detected |
| Example 20 | Bismuth oxide | $5 \times 10^{-8}$ | 262 | None | Not detected |
| Example 21 | Bismuth nitrate pentahydrate | $5 \times 10^{-7}$ | 308 | None | Not detected |
| Example 22 | Bismuth oxyacetate | $5 \times 10^{-6}$ | 463 | None | Not detected |

*(Weight of bismuth as metal)/(Weight of toluene plus acetic acid)
**Deterioration in STY in 300 hours of reaction relative to initial STY

TABLE 8

|  | Catalyst | Pore[1] structure | DVB[2] (wt %) | Acid[3] quantity (mg eq.) | Total[4] exchange capacity (m eq./g) | BC[5] (%) | BS[6] (%) |
|---|---|---|---|---|---|---|---|
| Example | | | | | | | |
| 28 | Amberlist 31 (Organo) | Gel | 4 | 47 | 4.8 | 49 | 100 |
| 29 | PK208H (Mitsubishi Chem) | MP | 4 | 47 | 4.6 | 49 | 100 |
| 30 | XT-2071 (Organo) | MR | 7 | 47 | 5.0 | 47 | 100 |
| Comparative Example | | | | | | | |
| 8 | Amberlite 120H (Organo) | Gel | 8 | 50 | 4.7 | 38 | 100 |
| 9 | SK1BH (Mitsubishi Chem.) | Gel | 8 | 52 | 4.9 | 37 | 100 |
| 10 | Amberlite 124H (Organo) | Gel | 12 | 45 | 4.7 | 20 | 100 |
| 11 | Amberlist 15 (Organo) | MR | 20 | 47 | 4.7 | 21 | 100 |

[1]Gel: Simple gel type structure
MP (Macroporous): Enlarged network structure
MR (Macroreticular): Porous structure
[2]DVB: Divinylbenzene unit content
[3]Acid quantity: Total of sulfonic acid group contained in catalyst
[4]Total exchange capacity: Total exchange capacity per unit weight of catalyst (dry resin)
[5]BC: Conversion ratio of benzyl acetate
[6]BS: Selectivity of benzyl alcohol

TABLE 9

|  | Starting material composition (wt %) BzOAc/Water/Acetic acid | BC[1] % | Equilibrium conversion ratio % | STY[3] g/L/h | BS[4] % | BzOBz[5] ppm | W/B[6] |
|---|---|---|---|---|---|---|---|
| Example | | | | | | | |
| 31 | 78.9/16.2/5.0 | 44.4 | 45.2 | 119 | 100.0 | 172 | 0.5 |
| 32 | 63.0/27.0/10.0 | 52.3 | 55.6 | 112 | 100.0 | 158 | 1.0 |
| 33 | 45.0/35.0/20.0 | 54.7 | 58.2 | 83 | 100.0 | 485 | 1.8 |
| 34 | 38.5/47.0/14.5 | 61.2 | 69.6 | 80 | 100.0 | 352 | 2.6 |
| 35 | 83.0/17.0/0.0 | 47.0 | 49.7 | 114 | 100.0 | 183 | 0.4 |
| Comparative Example | | | | | | | |
| 12 | 92.9/7.1/0.0 | 30.1 | 30.4 | 95 | 99.7 | 3008 | 0.2 |
| 13 | 49.0/11.8/39.2 | 21.4 | 24.0 | 36 | 99.9 | 502 | 1.4 |
| 14 | 30.0/60.0/10.0 | 64.8 | 79.5 | 66 | 100.0 | 275 | 3.9 |

[1]BC: Conversion ratio of banzyl acetate
[2]Equilibrium convertion ratio: Estimated value for equilibrium constant K = 0.40
[3]STY: Reaction productivity of grams of benzyl alcohol per hour per liter of wet catalyst
[4]BS: Selectivity of benzyl alcohol
[5]BzOBz: Mole ratio of by-product benzyl ether to benzyl alcohol
[6]W/B: Weight ratio of water to benzyl alcohol in liquid product: Index of load in separatio-recovery process

What is claimed is:

1. A process for producing benzyl alcohol of high purity by hydrolysis of benzyl acetate in the presence of a solid acid catalyst, comprising steps of feeding benzyl acetate, water, and acetic acid to a hydrolysis reactor packed with a solid acid catalyst to cause reaction to obtain a liquid reaction mixture containing benzyl acetate, water, benzyl alcohol, and acetic acid; introducing the liquid reaction mixture to an acetic acid-water recovery column to separate the liquid reaction mixture by distillation into a column top distillate composed of acetic acid and water and a column bottom liquid composed mainly of benzyl alcohol and benzyl acetate; recycling the column top distillate of the acetic acid-water recovery column, after removing most of the acetic acid by an acetic acid-water separation column, to the hydrolysis reactor.

2. The process for producing benzyl alcohol of high purity according to claim 1, wherein the column bottom liquid of the acetic acid-water recovery column is distilled in an alcohol concentration column to obtain a column top fraction composed of benzyl alcohol and benzyl acetate and a column bottom fraction composed of benzyl acetate, and the column bottom fraction of the alcohol concentration column is recycled to the hydrolysis reactor.

3. The process for producing benzyl alcohol of high purity according to claim 2, wherein benzyl alcohol is obtained from the column top fraction of the alcohol concentration column.

4. The process for producing benzyl alcohol of high purity according to claim 2, wherein the column top fraction of the alcohol concentration column is mixed with additional water, and the mixture is distilled by a first alcohol purification column to obtain a column top distillate composed of benzyl acetate, benzyl alcohol, and water, and a column bottom liquid composed of water-containing benzyl alcohol; the column top distillate of the first alcohol concentration column is separated by a liquid-liquid separator into an organic phase composed of benzyl acetate and benzyl alcohol and an aqueous phase; the organic phase is recycled to the acetic acid-water recovery column or the hydrolysis reactor; and the aqueous phase is recycled to the first alcohol purification column.

5. The process for producing benzyl alcohol of high purity according to claim 4, wherein the column bottom liquid of the first alcohol purification column is distilled by a second alcohol purification column to obtain benzyl alcohol from the column bottom; and the column top distillate composed of water and benzyl alcohol is recycled to the first alcohol purification column.

6. The process for producing benzyl alcohol of high purity according to claim 2, wherein the column top distillate of the alcohol concentration column is distilled with glycerin by an extractive distillation column to obtain a column top fraction composed of benzyl acetate, and benzyl alcohol, and a column bottom fraction composed of glycerin-containing benzyl alcohol; the column top fraction of the extractive distillation column is mixed with additional water, and is separated by a liquid-liquid separator into an organic phase composed of benzyl acetate and benzyl alcohol and an aqueous phase; the organic phase is recycled to the hydrolysis reactor; and the aqueous phase is recycled to the extractive distillation column.

7. The process for producing benzyl alcohol of high purity according to claim 6, wherein the column bottom fraction obtained by the extractive distillation column is distilled by a product column to obtain benzyl alcohol from the column top; and a column bottom fraction mainly composed of glycerin is recycled to the extractive distillation column.

8. A process for producing benzyl alcohol by hydrolysis of benzyl acetate in the presence of a solid acid catalyst, wherein the solid acid catalyst is a sulfonated styrene-divinylbenzene copolymer of a divinylbenzene unit content of less than 8% by weight.

9. A process for producing benzyl alcohol by hydrolysis of benzyl acetate in the presence of a sulfonic acid group-containing cation exchange resin, wherein the starting material comprises benzyl acetate (x % by weight), water (y % by weight), and acetic acid (z % by weight) in the range:

$1/9 \leq y/x \leq 3/2$, and $0 \leq z \leq 30$ $(x+y+z=100)$.

10. The process for producing benzyl alcohol according to claim 9, wherein the starting material has composition in the range:

$1/9 \leq y/x \leq 2/3$, and $0 \leq z \leq 20$.

11. A process for producing benzyl alcohol of high purity by transesterification of benzyl acetate with methanol in the presence of a basic catalyst, wherein benzyl acetate is fed to an upper portion of a reaction-distillation column and methanol is fed at a lower portion of the reaction-distillation column, bringing benzyl acetate and methanol into contact with each other countercurrently in the presence of the basic catalyst to obtain a column top distillate composed mainly of methyl acetate and methanol, and a column bottom liquid composed mainly of methanol and benzyl alcohol; the column bottom liquid of the reaction-distillation column is introduced to a methanol separation column to obtain a column top fraction composed mainly of methanol, and a column bottom fraction composed mainly of benzyl alcohol; the column top fraction of the methanol separation column is recycled to the reaction-distillation column; and the column bottom liquid is introduced to an alcohol purification column to obtain benzyl alcohol by distillation.

12. The process for producing benzyl alcohol of high purity according to claim 11, wherein the column bottom fraction of the methanol separation column is introduced to a solid separator to remove a solid matter therefrom, and then introduced to the alcohol purification column.

13. The process for producing benzyl alcohol of high purity according to claim 11 or claim 12, wherein the column top distillate of the reaction-distillation column is introduced to an extractive distillation column to obtain a column bottom liquid composed mainly of water and methanol; the column bottom liquid is introduced to a methanol recovery column for distillation to obtain a column top fraction composed mainly of methanol and a column bottom fraction composed mainly of water, the column top fraction is recycled to the reaction-distillation column, and the column bottom fraction is recycled to the extractive distillation column.

14. The process for producing benzyl alcohol of high purity according to claim 13, wherein the column top fraction of the extractive distillation column composed mainly of water and methyl acetate is introduced to a hydrolysis reactor, and methyl acetate is hydrolyzed by addition of water in the presence of an acidic catalyst to obtain a hydrolysis mixture; the hydrolysis mixture is introduced to a methyl acetate recovery column for distillation to obtain a column top liquid composed mainly of methyl acetate and methanol, and a column bottom liquid; the column top liquid is recycled to the extractive distillation column; the column bottom liquid is introduced to an acetic acid recovery column for distillation, and a column top distillate composed mainly of water is recycled to the hydrolysis reactor.

* * * * *